(12) United States Patent
Park et al.

(10) Patent No.: US 9,120,814 B2
(45) Date of Patent: Sep. 1, 2015

(54) COMPOUNDS WITH EMBEDDED BENZOPYRAN MOTIF FOR CORE STRUCTURES AND PREPARATION METHOD THEREOF

(75) Inventors: Seung Bum Park, Seoul (KR); Hwan Jong Jang, Seoul (KR); Sung Kon Ko, Seoul (KR); EunHa Kim, Seoul (KR); Sangmi Oh, Siheung-si (KR); Jongmin Park, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 1075 days.

(21) Appl. No.: 12/481,137

(22) Filed: Jun. 9, 2009

(65) Prior Publication Data

US 2009/0326015 A1 Dec. 31, 2009

Related U.S. Application Data

(63) Continuation-in-part of application No. PCT/KR2006/005441, filed on Dec. 13, 2006.

(30) Foreign Application Priority Data

Dec. 13, 2006 (KR) .................. 10-2006-0127039

(51) Int. Cl.
C07D 403/04 (2006.01)
C07D 491/052 (2006.01)
C07D 311/04 (2006.01)
C07D 491/107 (2006.01)
C07D 491/147 (2006.01)
C07D 491/20 (2006.01)

(52) U.S. Cl.
CPC .......... *C07D 491/052* (2013.01); *C07D 311/04* (2013.01); *C07D 491/107* (2013.01); *C07D 491/147* (2013.01); *C07D 491/20* (2013.01)

(58) Field of Classification Search
None
See application file for complete search history.

(56) References Cited

U.S. PATENT DOCUMENTS 4,971,982 A * 11/1990 Attwood et al. .............. 514/337
6,077,850 A * 6/2000 Carter et al. .................. 514/311
2005/0176750 A1* 8/2005 Cai et al. ...................... 514/291

FOREIGN PATENT DOCUMENTS

GB 1389822 A * 12/1972
GB 1321296 A * 6/1973
GB 1322938 * 7/1973

OTHER PUBLICATIONS

Cacchi et al. Journal of Molecular Catalysis A: Chemical, 2004, vol. 214, pp. 57-64.*
International Search Report for PCT/KR2006/005441 dated Sep. 10, 2007.
Ko et al., "Concise and diversity-oriented synthesis of novel scaffolds embedded with privileged benzopyran motif", Chem. Commun., 2006, pp. 2962-2964.
Colotin et al., "Diels-alder polycycloadducts obtained from new bis-benzopyrones and biz-maleimides", Analele Stiintifice Ale Universitatii "AL.I.Cuza" Iasi, 2004, pp. 71-76.
Soliman et al., "Relative reactivity of benzopyranone and isobenzofurodione rings in isobezofuro [4,5-C] bezopyrantrione", Anales de Quimica, 1991, vol. 87, pp. 895-898.

* cited by examiner

*Primary Examiner* — Samira Jean-Louis
(74) *Attorney, Agent, or Firm* — Hamre, Schumann, Mueller & Larson, P.C.

(57) ABSTRACT

The present invention relates to a compound having benzopyran core, a preparation method of the derivatives by liquid phase synthesis and solid phase synthesis through diversity-oriented synthesis, and an anticancer agent comprising the compound that exhibit excellent cytotoxicity against cancer cells.

3 Claims, 2 Drawing Sheets

COMPOUNDS WITH EMBEDDED BENZOPYRAN MOTIF FOR CORE STRUCTURES AND PREPARATION METHOD THEREOF

CROSS-REFERENCE TO RELATED APPLICATIONS

This application is a continuation-in-part of international application No. PCT/KR2006/005441, filed Dec. 13, 2006, which claims the benefit of Korean patent application No. 10-2006-0127039 filed Dec. 13, 2006. The disclosures of said applications are incorporated by reference herein.

FIELD OF THE INVENTION

The present invention relates to a compound having benzopyran core, a preparation method thereof by liquid phase synthesis and solid phase synthesis through diversity-oriented synthesis, and an anticancer agent comprising the compound that exhibit excellent cytotoxicity against cancer cells.

BACKGROUND OF THE INVENTION

Traditional synthetic organic chemistry has been developed with the development of target oriented synthesis. Many organic chemists have been engaged in the investigation and development of new reactions in the synthesis of various natural products. In the target oriented synthesis, a specific natural product is targeted, and then synthesized. Thus, the obtained compound can be represented by one point as the distribution in chemical space. Therefore, it can be said that target oriented synthesis is very limited in terms of the diversity of compound.

Accordingly, many efforts have been made to improve specific chemical properties of the compound and track down the more biologically active compound, which results in the development of combinatorial chemical synthesis.

Combinatorial chemical synthesis is a new synthetic method in the development of new materials. While the conventional organic synthesis methods can synthesize one kind of compound via a single reaction, the combinatorial chemical synthetic technique is a highly efficient method which can synthesize more various and numerous compounds at the same time or automate the multi-step synthetic process. With the technique, it has become easier to screen a biological hit compound and a lead compound having a new structure, and optimize structure and activity thereof. Combinatorial chemical synthesis has been mainly studied in medicinal chemistry, in particular, contributed to the study of structure-activity relationship, and the skeletal diversity can be ensured via various substitution reactions in a specific structure.

Diversity-oriented synthesis is a new concept in organic synthesis, where the aim is to synthesize collections of structurally-diverse compounds that are broadly distributed in the chemical space, and search for a variety of new biologically active compounds by High Throughput Screening.

In diversity-oriented synthesis, compounds having different core skeletons can be prepared at the same time, and constructed as a library. Thus, a larger number of different active compounds can be identified from the library by various search methods.

If the concept of privileged structure is introduced to the diversity-oriented synthesis, it is very advantageous to search biologically active compounds.

The term "privileged structure" is defined as a single molecular framework contained in many natural products or biologically active molecules. The application of the privileged structure to diversity-oriented synthesis has been attempted over a long period of time. In particular, benzodiazepine is a privileged structure that had been frequently applied to the synthesis by many early chemists, and synthesized by many groups with great interest. The most famous example thereof is a library synthesized by Nicolaou group.

Benzopyran is a privileged structural motif observed in many biologically active natural products, and it plays an important role in binding with various biopolymers. To date, synthesis of bioactive benzopyrans has been extensively studied, especially a combinatorial library based on a privileged benzopyran template has been reported by Nicolaou and coworkers (K. C. Nicolaou and H. J. Mitchell, *J. Am. Chem. Soc.*, 2000, 122, 9939; Y. D. Gong and S. E. Yoo, *J. Comb. Chem.*, 2003, 5, 577; J. Y. Hwang and Y. D. Gong, *J. Org. Chem.*, 2005, 70, 10151; K. C. Nicolaou and J. A. Prefferkorn, *Org. Biomol. Chem.*, 2003, 1, 908; K. Sivakumar and Q. Wang, *Org. Let.*, 2004, 6, 4603; V. A. Ashwood and K. Willcocks, *J. Med. Chem.*, 1986, 29, 2194; R. Bergmann and R. Gericke, *J. Med. Chem.*, 1990, 33, 2759). However, previous reports focused on partial, limited diversifications via substitution for the arene region of benzopyrans by solid phase synthesis.

Natural products and synthetic products having benzopyran skeletons display antioxidant activity. Therefore, benzopyran has been widely known as skeletons for the development of compounds having pharmacological effects such as therapeutic agents for neurological diseases, hypertensions, and diabetes, and extensively utilized.

Accordingly, the present inventors have made extensive studies on compounds having skeletal diversity with a privileged benzopyran substructure through the branching pathway via various chemical transformations such as Diels-Alder reaction, click chemistry, and palladium mediated cross-coupling. Further, they applied diversity-oriented synthesis to the resultants, and synthesized compounds having benzopyran core through the reconstruction of core skeletons in the pyran region, not through the partial, limited modification via substitution for the arene region of benzopyrans. They found that the compounds exhibit excellent cytotoxicity against cancer cells, thereby completing the present invention.

SUMMARY OF THE INVENTION

The present invention provides a compound having benzopyran core.

Further, the present invention provides a preparation method for the compound having benzopyran core by liquid phase synthesis.

Further, the present invention provides a preparation method for the compound having benzopyran core by solid phase synthesis.

Further, the present invention provides an anticancer agent comprising the compound having benzopyran core as an active ingredient.

In order to achieve the objects, the present invention provides a compound having benzopyran core, represented by any one of the following Formulae 1 to 10:

[Formula 1]
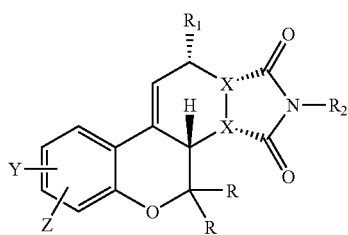

[Formula 2]
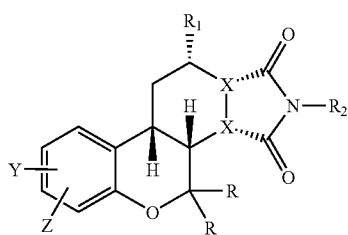

[Formula 3]
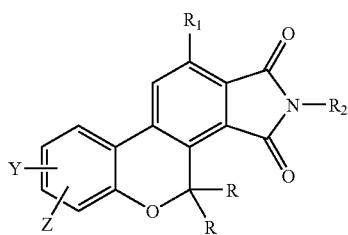

[Formula 4]
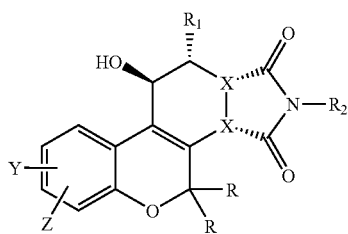

In Formulae 1 to 4 each Y and Z independently are hydrogen; C1 to C6 linear or branched alkyl; hydroxy; protected hydroxy in the form of C3 to C9 linear or branched alkyl silyl ether; halogen; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, protected hydroxy in the form of C3 to C9 linear or branched alkyl silyl ether, halogen, amino, C1 to C4 alkylamino, C1 to C4 dialkylamino, acetyl and benzoyl, $R_1$ is hydrogen; methoxymethyl, C1 to C6 linear or branched alkyl; benzyl; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, halogen, amino, C1 to C4 alkylamino, C1 to C4 dialkylamino, acetyl and benzoyl, $R_2$ is hydrogen; hydroxy; C1 to C6 linear or branched alkyl; halogen; benzyl; C3 to C6 cycloalkyl; phenylamino; aminocarbonyl; methoxycarbonyl; C1 to C6 linear or branched carboxylic acid; thiophenylmethyl; N-benzylpiperidinyl; or phenyl that is substituted or unsubstituted with at least one substituent selected from the group consisting of C1 to C6 linear or branched alkyl, C1 to C6 linear or branched alkoxy, hydroxy, halogen, amino, C1 to C4 alkylamino, C1 to C4 dialkylamino, phenylamino, acetyl, benzoyl, phenyldiazo, carboxyl, benzoxazolyl, nitro, morpholinyl and $CF_3$, each R independently is methyl, or two of Rs together form —$CH_2(CH_2)_2CH_2$—, and X is CH or N.

[Formula 5]
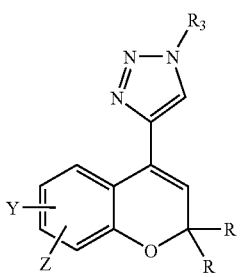

In Formula 5 each Y and Z independently are hydrogen; C1 to C6 linear or branched alkyl; hydroxy; protected hydroxy in the form of C3 to C9 linear or branched alkyl silyl ether; halogen; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, protected hydroxy in the form of C3 to C9 linear or branched alkyl silyl ether, halogen, amino, C1 to C4 alkylamino, C1 to C4 dialkylamino, acetyl and benzoyl, $R_3$ is C1 to C8 linear or branched alkyl; C3 to C6 cycloalkylmethyl; pyridylmethyl; phenyl substituted or unsubstituted with at least one halogen; triazine substituted with methylsulfinyl or isopropylamino; C1 to C8 hydroxyalkyl; linear or branched carboxylic acid containing C1 to C8 heteromolecule; benzyl that is substituted or unsubstituted with at least one substituent selected from the group consisting of C1 to C6 linear or branched alkyl, C1 to C6 linear or branched alkoxy methylthio, hydroxy, halogen, nitrile, acetyl, benzoyl and carboxylic acid;

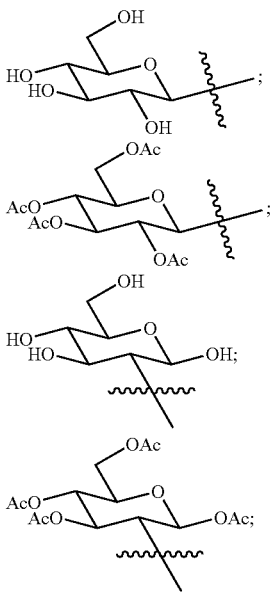

-continued

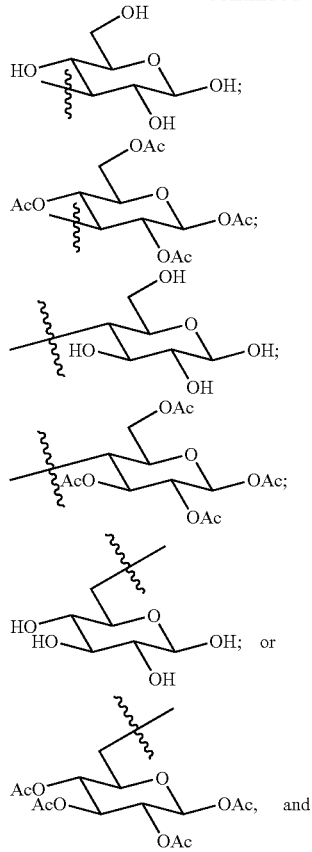

each R independently is methyl, or two of Rs together form —CH$_2$(CH$_2$)$_2$CH$_2$—.

[Formula 6]

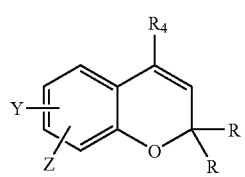

In Formula 6,
each Y and Z independently are hydrogen; C1 to C6 linear or branched alkyl; hydroxy; protected hydroxy in the form of C3 to C9 linear or branched alkyl silyl ether; halogen; C1 to C6 linear or branched alkoxy; or phenyl that is substituted or substituted with at least one substituent selected from the group consisting of C1 to C6 linear or branched alkyl, C1 to C6 linear or branched alkoxy, hydroxy, protected hydroxy in the form of C3 to C9 linear or branched alkyl silyl ether, halogen, amino, C1 to C4 alkylamino, C1 to C4 dialkylamino, acetyl and benzoyl, R$_4$ is pyridinyl; thiophenyl; dimethylpyrazolyl; furyl; dibenzofuryl; thianthrenyl; or phenyl that is substituted or unsubstituted with at least one substituent selected from the group consisting of C1 to C6 linear or branched alkyl, C1 to C6 linear or branched alkoxy, phenoxy, benzyloxy, C1 to C6 linear or branched alkylsulfinyl, hydroxy, C1 to C6 linear or branched hydroxyalkyl, halogen, amino, C1 to C4 alkylamino, C1 to C4 dialkylamino, acetyl, benzoyl, formyl, nitro, nitrile and CF$_3$, and each R independently is methyl, or two of Rs together form —CH$_2$(CH$_2$)$_2$CH$_2$—.

[Formula 7]

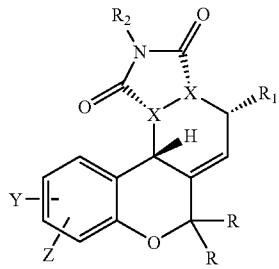

[Formula 8]

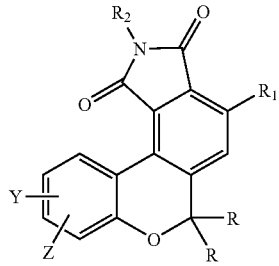

In Formulae 7 and 8,
each Y and Z independently are hydrogen; C1 to C6 linear or branched alkyl; hydroxy; protected hydroxy in the form of C3 to C9 linear or branched alkyl silyl ether; halogen; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, protected hydroxy in the form of C3 to C9 linear or branched alkyl silyl ether, halogen, amino, C1 to C4 alkylamino, C1 to C4 dialkylamino, acetyl and benzoyl, R$_1$ is hydrogen; methoxymethyl; C1 to 66 linear or branched alkyl; benzyl; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, halogen, amino, C1 to C4 alkylamino, C1 to C4 dialkylamino, acetyl and benzoyl, R$_2$ is hydrogen; hydroxy; C1 to C6 linear or branched alkyl; halogen; benzyl; C3 to C6 cycloalkyl; phenylamino; aminocarbonyl; methoxycarbonyl; C1 to C6 linear or branched carboxylic acid, thiophenylmethyl; N-benzylpiperidinyl; or phenyl that is substituted or unsubstituted with at least one substituent selected from the group consisting of C1 to C6 linear or branched alkyl, C1 to C6 linear or branched alkoxy, hydroxy, halogen, amino, C1 to C4 alkylamino, C1 to C4 dialkyl-amino, phenylamino, acetyl, benzoyl, phenyldiazo, carboxyl, benzoxazolyl, nitro, morpholinyl and CF$_3$, each R independently is methyl, or two of Rs together form —CH$_2$(CH$_2$)$_2$CH$_2$—, and X is CH or N.

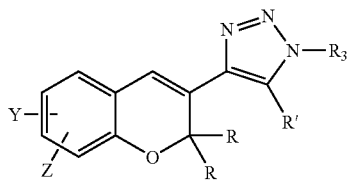

[Formula 9]

In Formula 9, each Y and Z independently are hydrogen; C1 to C6 linear or branched alkyl; hydroxy; protected hydroxy in the form of C3 to C9 linear or branched alkyl silyl ether, halogen; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, protected hydroxy in the form of C3 to C9 linear or branched alkyl silyl ether, halogen, amino, C1 to C4 alkylamino, C1 to C4 dialkyl amino, acetyl and benzoyl, $R_3$ is C1 to C8 linear or branched alkyl; C3 to C6 cycloalkylmethyl; pyridylmethyl; phenyl substituted or unsubstituted with at least one halogen; triazine substituted with methylsulfinyl or isopropylamino; C1 to C8 hydroxyalkyl; linear or branched carboxylic acid containing C1 to C8 heteromolecule; benzyl that is substituted or unsubstituted with at least one substituent selected from the croup consisting of C1 to C6 linear or branched alkyl, C1 to C6 linear or branched alkoxy, methylthio, hydroxy,

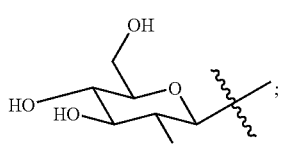

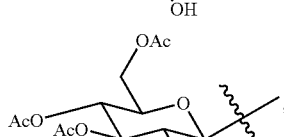

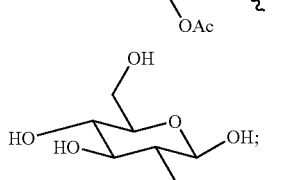

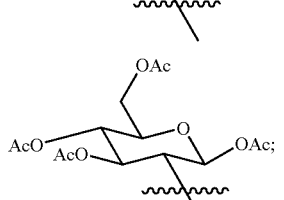

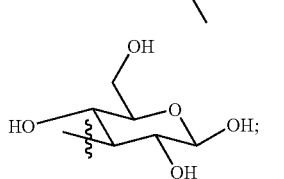

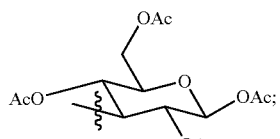

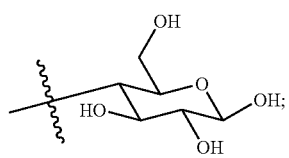

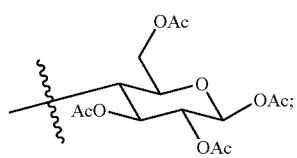

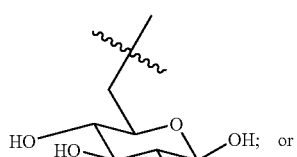

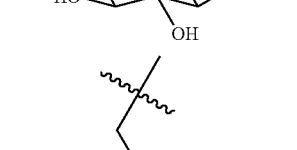

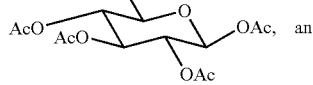

R' is hydrogen; C6 to C4 alkyl; or alkoxy, and each R independently is methyl, or two of Rs together form —$CH_2(CH_2)_2CH_2$—.

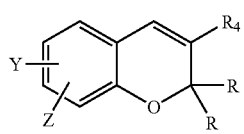

[Formula 10]

In Formula 10, each Y and Z independently are hydrogen; C1 to C6 linear or branched alkyl; hydroxy; protected hydroxy in the form of C3 to C9 linear or branched alkyl silyl ether; halogen; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, protected hydroxy in the form of C3 to C9 linear or branched alkyl silyl ether, halogen, amino, C1 to C4 alkylamino, C1 to C4 dialkylamino, acetyl and benzoyl, $R_4$ is pyridinyl; thiophenyl; dimethylpyrazolyl; furyl; dibenzofuryl; thianthrenyl; or phenyl that is substituted or unsubstituted with at least one substituent selected from the group consisting of C1 to C6 linear or branched alkyl, C1 to C6 linear or branched alkoxy, phenoxy, benzyloxy, C1 to C6 linear or branched alkylsulfinyl, hydroxy, C1 to C6 linear or branched hydroxyalkyl, halogen, amino, C1 to C4 alkylamino, C1 to C4 dialkylamino, acetyl, benzoyl, formyl, nitro, nitrile and $CF_3$, and each R independently is methyl, or two of Rs together form —$CH_2(CH_2)_2CH_2$—.

Further, the present invention provides a preparation method for the compound having benzopyran core, represented by any one of the following Formulae 1 to 10, by liquid phase synthesis.

Further, the present invention provides a preparation method for the compound having benzopyran core, represented by any one of the following Formulae 1 to 10, by solid phase synthesis.

Further, the present invention provides an anticancer agent comprising the compound having benzopyran core, represented by any one of the following Formulae 1 to 10, as an active ingredient.

Analogs of the natural product being useful to organisms can be simply synthesized by using or modifying a preparation method of the compound having benzopyran core of the present invention by liquid phase synthesis and solid phase synthesis, and the compound having benzopyran core exhibit excellent cytotoxicity against cancer cells, thereby being used as an anticancer agent.

BRIEF DESCRIPTION OF THE DRAWINGS

The above and other features and advantages of the present invention will become more apparent by describing in detail preferred embodiments thereof with reference to the attached drawings in which.

DETAILED DESCRIPTION OF THE INVENTION

Figure 1:
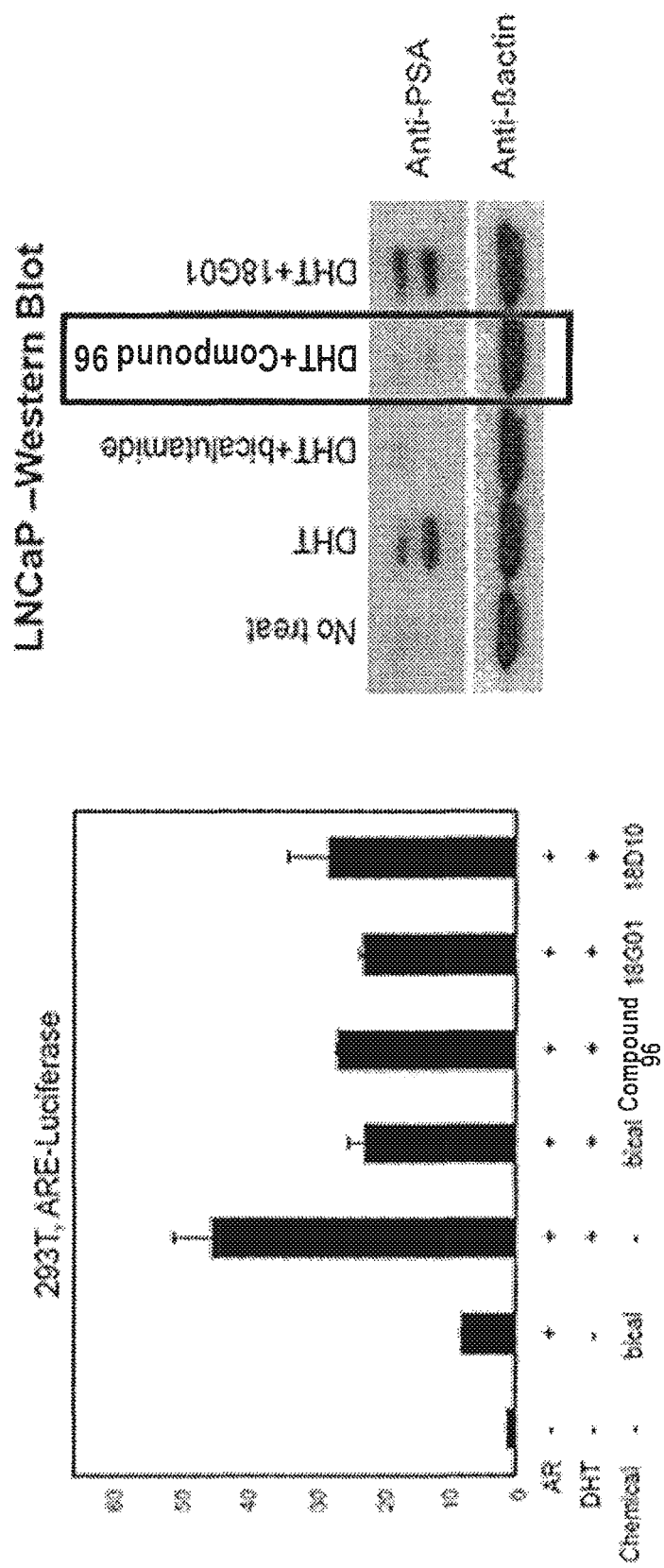
FIG. 1 shows an experimental result of western blot analysis which demonstrates anticancer activity based on the expression amount of prostate specific antigen (PSA) as a target protein of androgen receptor, after deriving a compound 96 (Formula 4) from LNCaP cell of androgen-dependent human prostate cancer cell line via screening by using luciferase assay system.

Hereinafter, the present invention will be described in more detail.

The present invention provides a compound having benzopyran core represented by any one of Formulae 1 to 10, a preparation method of the compound having benzopyran core by liquid phase synthesis and solid phase synthesis, and an anticancer agent comprising the compound.

The compound having benzopyran core represented by any one of Formulae 1 to 10 according to the present invention can be prepared by the following liquid phase synthesis.

There are two kinds of the liquid phase synthesis of the compound having benzopyran core according to the present invention, Reaction I and Reaction II, depending on intermediate compound synthesized in each initial reaction. The Reaction I according to the present invention may be, but not limited thereto, Reaction I-1, Reaction I-2, or Reaction I-3, comprising two-steps of the following Reactions (a) and (b-1), Reactions (a) and (b-2), and Reactions (a) and (b-3), respectively. The Reaction II according to the present invention may be Reaction II-1. Reaction II-2, and Reaction II-3, comprising two-steps of the following Reactions (c) and (d-1), Reactions (c) and (d-2), and Reactions (c) and (d-3), respectively.

A compound represented by any one of Formulae 1 to 4 can be prepared by Reaction I-1, a compound represented by Formula 5 can be prepared by Reaction I-2, and a compound represented by Formula 6 can be prepared by Reaction I-3. Further, a compound represented by any one of Formulae 7 and 8 can be prepared by Reaction II-1, a compound represented by Formula 9 can be prepared by Reaction II-2 and a compound represented by Formula 10 can be prepared by Reaction I-3.

In this connection, a step of removing a triisopropylsilyl (TIPS) protecting group is contained in each step of Reactions (b-1), (b-2), (b-3), (d-1), (d-2), and (d-3). There are two methods of removing the TIPS protecting group. As one method, the protecting group is treated with TBAF (tetra-n-butylammonium fluoride, 1.1 to 1.3 equivalent weights), and subjected to reaction with tetrahydrofuran as a solvent for 1 to 2 hours. As the other method, hydrogen fluoride and pyridine are dissolved in tetrahydrofuran in a volume ratio of 5:5:90. Then, the protecting group is treated with the solution for 2 to 4 hours, and then quenched with ethoxytrimethylsilane.

The liquid phase synthesis of a compound represented by any one of Formulae 1 to 6 according to the present invention will be described with reference to the following Reactions, Reaction (a) and at least one selected from Reactions (b-1) to Reaction (b-3). However, the scope of the present invention is not limited by these Reactions.

A preparation method for the compound of the present invention according to the following Reactions (a) and (b-1), Reactions (a) and (b-2), or Reactions (a) and (b-3), comprising the steps of:

Reaction (a) preparing an intermediate compound 3a (intermediate compound 3b) through a series of reactions using 2,4-dihydroxyacetophenone as a starting material, and then Reaction (b-1) preparing a compound 4a (compound 4b), a compound 9a (compound 9b), a compound 10a (compound 10b) and a compound 11a (compound 11b) by reacting the compound 3a (compound 3b) with vinyltin and maleimide, and then subjecting to at least one selected from hydrogenation, aromatization and epoxidation;

Reaction (b-2) preparing a compound 14a (compound 14b) by reacting the compound 3a (compound 3b) with an azide compound; or Reaction (b-3) preparing a compound 16a (compound 16b) by reacting the compound 3a (compound 3b) with a boronic acid compound.

Each step of the liquid phase synthesis of the compound having benzopyran core according to the present invention will be described in detail as follows.

The intermediate compound 3a (intermediate compound 3b) of the compound represented by any one of Formulae 1 to 6 according to the present invention is prepared by the pathway represented by the following Reaction (a).

[Reaction (a)]

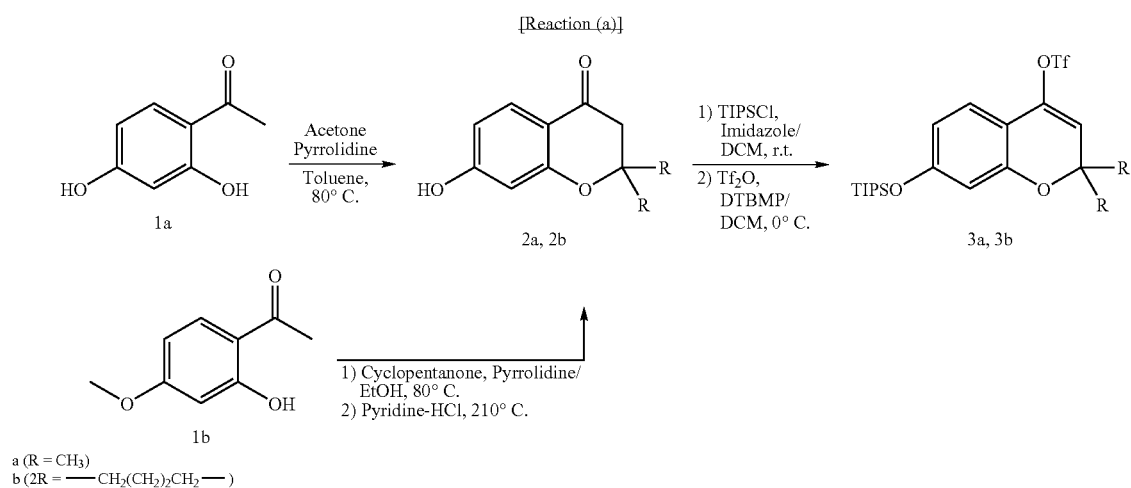

a (R = CH₃)
b (2R = —CH₂(CH₂)₂CH₂—)

wherein R is the same as defined in Formulae 1 to 6. That is, in the Reaction (a), a represents that each R independently is methyl group, and b represents that two of Rs together form —CH$_2$(CH$_2$)$_2$CH$_2$—.

2,4-Dihydroxyacetophenone (compound 1a), which is commercially available or can be easily prepared by a known method, is used as a starting material, acetone (10 equivalent weights) is added, and pyrrolidine (2.0 to 3.0 equivalent weights) that reacts with ketone of acetophenone to form imine and facilitates aldol reactions is added to prepare a compound 2a. At this time, in the case of using 2-hydroxy-4-methoxyacetophenone (compound 1b) as a starting material, cyclopentanone (1.5 to 2.0 equivalent weights) is first added to prepare intermediate compounds using pyrrolidine, followed by demethylation to prepare a compound 2b. Then, a hydroxy group of phenol in the compound 2a (compound 2b) is substituted with a TIPS protecting group using t-butyldimethylsilylchloride (TBSCl), trimethylsilylchloride (TMSCl) or triisopropylsilylchloride (TIPSCl), preferably TIPSCl (1.1 to 1.5 equivalent weights) at about 0 to 25° C., and reacted with trifluorosulfonyl anhydride (Tf$_2$O, 1.1 to 1.3 equivalent weights) that transforms ketone to vinyl triflate, and DTBMP (di-tert-butyl-4-methylpiridine, 1.1 to 1.3 equivalent weights) that acts as a base to facilitate the detachment of protons at about 0 to 25° C., so as to synthesize the compound 3a (compound 3b).

The compound represented by any one of Formulae 1 to 6 according to the present invention is prepared using the intermediate compound 3a (intermediate compound 3b) synthesized by Reaction (a) as a starting material in the pathway represented by the following Reaction, at least one selected from Reactions (b1) to (b-3).

Reaction I-1 which is the liquid phase synthesis of the compound having benzopyran core represented by any one of Formulae 1 to 4 according to the present invention, comprises the following Reaction (b-1), and will be described in detail as follow.

[Reaction (b-1)]

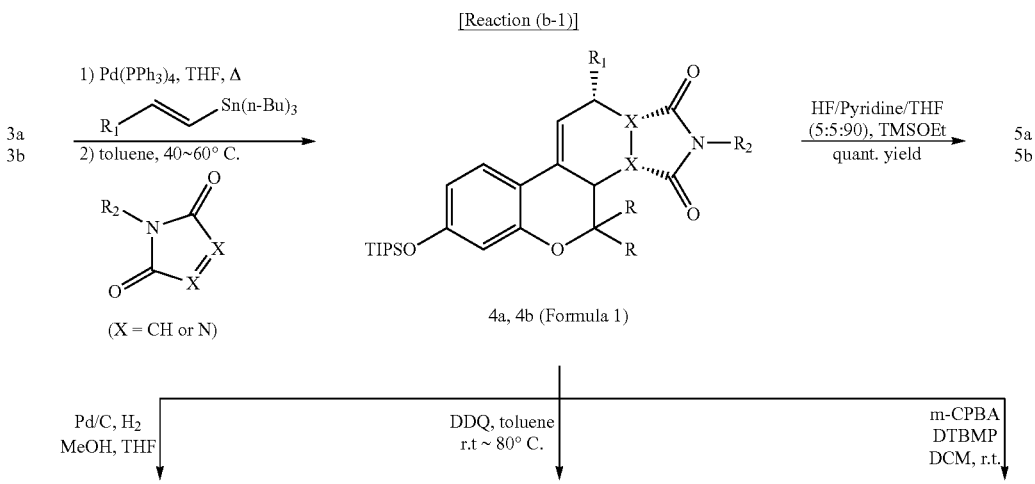

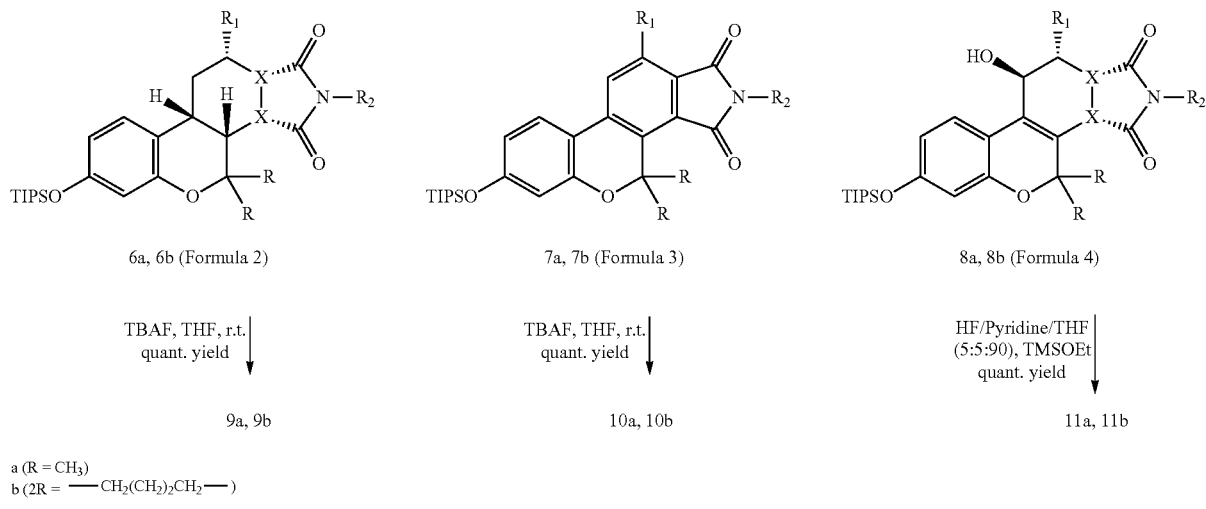

6a, 6b (Formula 2)      7a, 7b (Formula 3)      8a, 8b (Formula 4)

TBAF, THF, r.t.      TBAF, THF, r.t.      HF/Pyridine/THF
quant. yield      quant. yield      (5:5:90), TMSOEt
          quant. yield 9a, 9b      10a, 10b      11a, 11b a (R = CH$_3$)
b (2R = —CH$_2$(CH$_2$)$_2$CH$_2$—)

wherein each of R, R$_1$, R$_2$ and X is the same as defined in Formulae 1 to 4. In particular, in the Reaction (b-1), a represents that each R independently is methyl group, and b represents that two of Rs together form —CH$_2$(CH$_2$)$_2$CH$_2$—, Tributylvinyltin (1.1 equivalent weights) substituted with R$_1$ that binds to triflate of the compound 3a (compound 3b) prepared in Reaction (a) is added, followed by Stille cross coupling (P. Espinet and A. M. Echavarren, *Angew. Chem., Int.*, 2004, 43, 4704) using tetrakis(triphenylphosphine)palladium as a catalyst. Maleimide substituted with R$_2$ is added to the obtained intermediate, followed by Diels-Alder Reaction using toluene as a solvent to prepare the compound 4a (compound 4b). At this time, in Diels-Alder Reaction, a strong endo-selectivity of maleimide provides one selective isomer, thus the compound 4a (compound 4b) is synthesized as only one isomer.

The compound 4a (compound 4b) is subjected to hydrogenation using Pd/C (palladium complex: w/w 10%) as a catalyst while supplying hydrogen gas to prepare a compound 6a (compound 6b).

Further, the compound 4a (compound 4b) is treated with DDQ (2,3-dichloro-5,6-dicyanobenzoquinone, 2.0 to 3.0 equivalent weights) and subjected to reaction at a high temperature of 80° C. to prepare a compound 7a (compound 7b).

Finally, the compound 4a (compound 4b) is treated with m-CPBA (meta-chloroperberizoic acid, 2.0 equivalent weights), followed by epoxidation to prepare a compound 8a (compound 8b). In this connection, in the case of performing the reaction with only m-CPBA, aromatized compound 7a (compound 7b) is also prepared. Therefore, in order to prevent such side reaction, DTBMP (2.5 equivalent weights) is preferably added to carry out the reaction.

At this time, the obtained compound is not prepared in the form of epoxide, but in the form of allylic alcohol due to a distortion of a ring structure after epoxidation.

The TIPS protecting groups are removed from the compound 4a (compound 4b), compound 6a (compound 6b), compound 7a (compound 7b), and compound 8a (compound 8b) to prepare a compound 5a (compound 5b), a compound 9a (compound 9b), a compound 10a (compound 10b), and a compound 11a (compound 11b) respectively. The compound 4a (compound 4b), compound 6a (compound 6b), compound 7a (compound 7b), and compound 8a (compound 8b) are treated with TBAF (tetra-n-butylammonium fluoride, 1.1 equivalent weights) and subjected to reaction using tetrahydrofuran as a solvent for about 2 hours to remove the TIPS protecting groups. At this time, since the compound 4a (compound 4b) and compound 8a (compound 8b) are unstable than the compound 6a (compound 6b) and compound 7a (compound 7b), the TIPS protecting groups are preferably removed under a mild condition by treating with a solution, in which hydrogen fluoride and pyridine are dissolved in tetrahydrofuran in a volume ration of 5:5:90.

Reaction I-2, which is the liquid phase synthesis of the compound having benzopyran core represented by Formula 5 according to the present invention, comprises the following Reaction (b-2), and will be described in detail as follow.

[Reaction (b-2)]

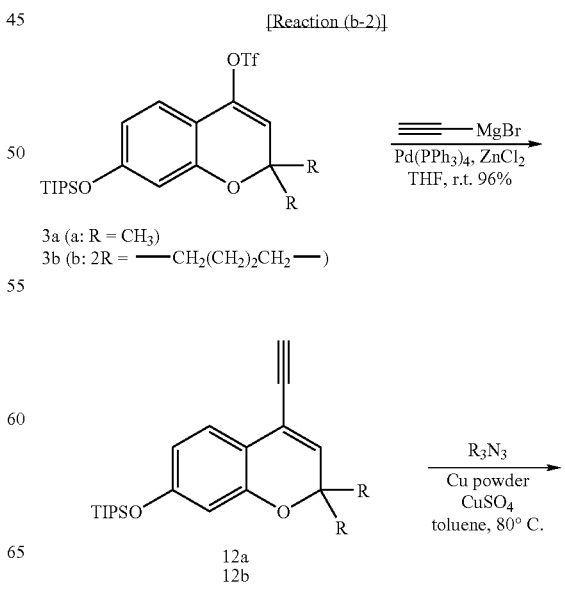

3a (a: R = CH$_3$)
3b (b: 2R = —CH$_2$(CH$_2$)$_2$CH$_2$—)

12a
12b

-continued

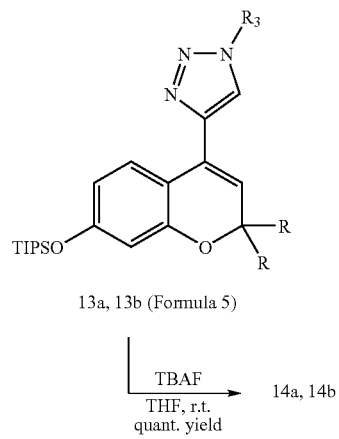

13a, 13b (Formula 5)

| TBAF
THF, r.t.
quant. yield → 14a, 14b wherein each of R and $R_3$ is the same as defined in Formula 5. In particular, in the Reaction (b-2), a represents that each R independently is methyl group, and b represents that two of Rs together form —$CH_2(CH_2)_2CH_2$—.

The OTf group of the compound 3a (compound 3b) prepared in Reaction (a) is substituted with an alkynyl group to prepare a compound 12a (compound 12b). Zinc chloride (2.5 equivalent weights) is added to alkynyl magnesium bromide (2 equivalent weights) to substitute magnesium with zinc, followed by Negishi cross coupling using tetrakis(triphenylphosphine)palladium as a catalyst to obtain the compound 12a (compound 12b).

An azide compound substituted with $R_3$ is added to the compound 12a (compound 12b), followed by click chemistry (L. V. Lee et al., *J. Am. Chem. Soc.*, 2003, 125, 9588; Z. P. Demko and K. B. Sharpless, *Angew. Chem. Int. Ed.*, 2002, 41, 2110) using copper sulfate as a catalyst to prepare a compound 13. The compound 13a (compound 13b) is reacted with TBAF (1.1 to 1.3 equivalent weights) at room temperature for 1 to 2 hours to remove the TIPS protecting groups, resulting in a compound 14a (compound 14b).

Reaction I-3, which is the liquid phase synthesis of the compound having benzopyran core represented by Formula 6 according to the present invention, comprises the following Reaction (b-3), and will be described in detail as follow.

-continued

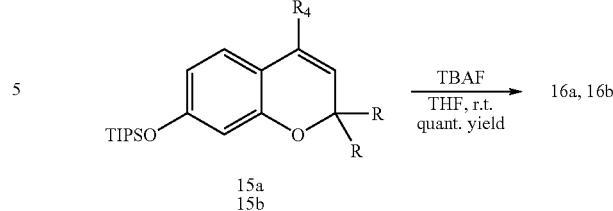

15a
15b

TBAF
THF, r.t.
quant. yield → 16a, 16b wherein each of R and $R_4$ is the same as defined in Formula 6. In particular, in the Reaction (b3), a represents that each R independently is methyl group, and b represents that two of Rs together form —$CH_2(CH_2)_2CH_2$—.

The compound 3a (compound 3b) prepared in Reaction (a) is reacted with a boronic acid compound substituted with $R_4$ to perform a Suzuki coupling reaction (S. R. Chemler and S. J. Danishefsky, *Angew. Chem. Int., Ed.*, 2001, 40, 4544; O. Takayuki and A. Suzuki, *J. Org Chem.*, 1993, 58, 2201; E. G. Occhiato et al. *J. Org. Chem.*, 2001, 66, 2459). At this time, a mixed solvent of ethanol and toluene (1:1) is used as a solvent, and tetrakis(triphenylphosphine)palladium is used as a catalyst. 10% sodium carbonate is added, and the reaction is carried out at 65° C. to prepare a compound 15a (compound 15b). TBAF (1.1 to 1.3 equivalent weights) is added thereto, and the reaction is carried out at 0 to 25° C. for 1 to 2 hours to remove the TIPS protecting group. Finally, a compound 16a (compound 16b) can be obtained.

The compound represented by any one of Formulae 7 to 10 according to the present invention can be prepared by the liquid phase synthesis of the following Reactions, Reaction (c) and at least one selected from Reactions (d-1) to (d-3).

A preparation method of the compound of the present invention according to Reactions (c) and (d-1), Reactions (c) and (d-2), or Reactions (c) and (d-3), comprising the steps of:

Reaction (c) preparing an intermediate compound 18a (intermediate compound 18b) through a series of reactions using 2,4-dihydroxyacetophenone as a starting material, and then Reaction (d-1) preparing a compound 20a (compound 20b) and a compound 22a (compound 22b) by reacting the compound 18a (compound 18b) with vinyltin aid maleimide, and then subjecting to reaction, e.g. aromatization;

Reaction (d-2) preparing a compound 25a (compound 25b) by reacting the compound 18a (compound 18b) with an azide compound; or Reaction (d-3) for preparing a compound 27a (compound 27b) reacting the compound 18a (compound 18b) with a boronic acid compound.

The intermediate compound 18a (intermediate compound 18b) of the compound represented by any one of Formulae 7 to 10 according to the present invention are prepared by the pathway represented by the following Reaction (c).

[Reaction (b-3)]

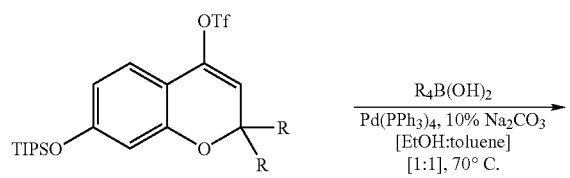

3a (a: R = $CH_3$)
3b (b: 2R = —$CH_2(CH_2)_2CH_2$—)

$R_4B(OH)_2$
$\xrightarrow{Pd(PPh_3)_4, 10\% Na_2CO_3}$
[EtOH:toluene]
[1:1], 70° C.

[Reaction (c)]

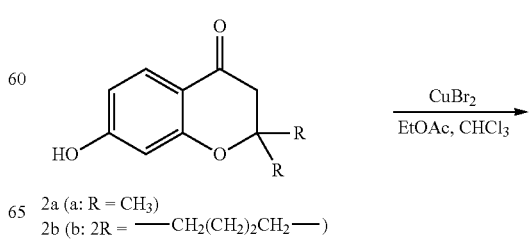

2a (a: R = $CH_3$)
2b (b: 2R = —$CH_2(CH_2)_2CH_2$—)

$\xrightarrow{CuBr_2}{EtOAc, CHCl_3}$

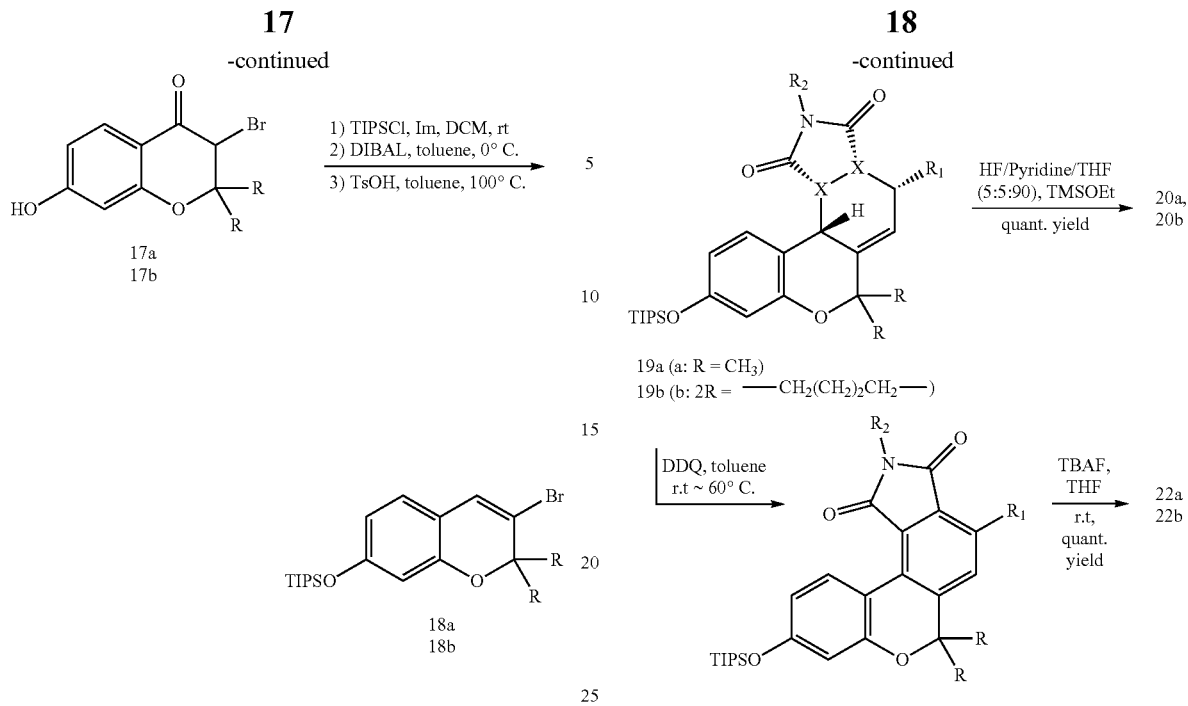

19a (a: R = CH$_3$)
19b (b: 2R = —CH$_2$(CH$_2$)$_2$CH$_2$—)

wherein R is the same as defined in Formulae 7 to 10. In particular, in the Reaction (c), a represents that each R independently is methyl group, and b represents that two of Rs together form —CH$_2$(CH$_2$)$_2$CH$_2$—.

In Reaction (c), the compound 2a (compound 2b) can be prepared in the same method as in Reaction (a). The compound 2a (compound 2b) is treated with copper bromide (1.5 to 2.0 equivalent weights), followed by bromination to obtain a compound 17a (compound 17b). A hydroxy group of phenol in the compound 17a (compound 17b) is substitute with a TIPS protecting group using TBSCl, TMSCl or TIPSCl, preferably TIPSCl (1.1 to 1.5 equivalent weights) at about 0 to 25° C., followed by reduction using DIBAL-H (diisobutylaluminum hydride, 2.0 to 3.0 equivalent weights) as a reducing agent at 0 to 25° C., so as to reduce ketone of the pyran region to alcohol. Then, the compound 17a (compound 17b) is treated with TsOH (p-toluenesulfonic acid, 10 mol %), followed by dehydration at about 80 to 100° C. to obtain a compound 18a (compound 18b).

Reaction II-1, which is the liquid phase synthesis of the benzopyran compound represented by Formulae 7 or 8 according to the present invention, comprises the following Reaction (d-1), and will be described in detail as follow.

[Reaction (d-1)]

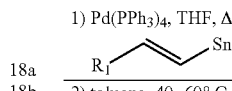

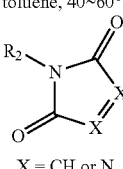

X = CH or N wherein each of R, R$_1$, R$_2$ and X is the same as defined in Formulae 7 and 8. In particular, in the Reaction (d-1), a represents that each R independently is methyl group, and b represents that two of Rs together form —CH$_2$(CH$_2$)$_2$CH$_2$—.

Tributylvinyltin (1.1 equivalent weights) substituted with R$_1$ that binds to triflate of the compound 18a (compound 18b) prepared in Reaction (c) is added, followed by Stille cross coupling (P. Espinet and A. M. Echavarren, *Angew. Chem., Int. Ed.*, 2004, 43, 4704) using tetrakis(triphenylphosphine) palladium as a catalyst. Maleimide substituted with R$_2$ is added to the obtained intermediate, followed by Diels-Alder Reaction using toluene as a solvent to prepare the compound 19a (compound 19b). At this time, in Diels-Alder Reaction, a strong endo-selectivity of maleimide provides one selective isomer, thus the compound 19a (compound 19b) is synthesized as only one isomer.

The compound 19a (compound 19b) is treated with DDQ (2.0 to 3.0 equivalent weights) and subjected to reaction at a high temperature of 60° C. to prepare a compound 21a (compound 21b).

Further, the TIPS protecting groups are removed from the compound 19a (compound 19b) and the compound 21a (compound 21b) to prepare a compound 20a (compound 20b) and a compound 22a (compound 22b) respectively. At this time, since the compound 19a (compound 19b) is unstable than the compound 21a (compound 21b), the TIPS protecting groups are preferably removed under a mild condition by treating with a solution, in which hydrogen fluoride and pyridine are dissolved in tetrahydrofuran in a volume ratio of 5:5:90.

Reaction II-2, which is the liquid phase synthesis of the benzopyran compound represented by Formula 9 according to the present invention, comprises the following Reaction (d-2), and will be described in detail as follow.

[Reaction (d-2)]

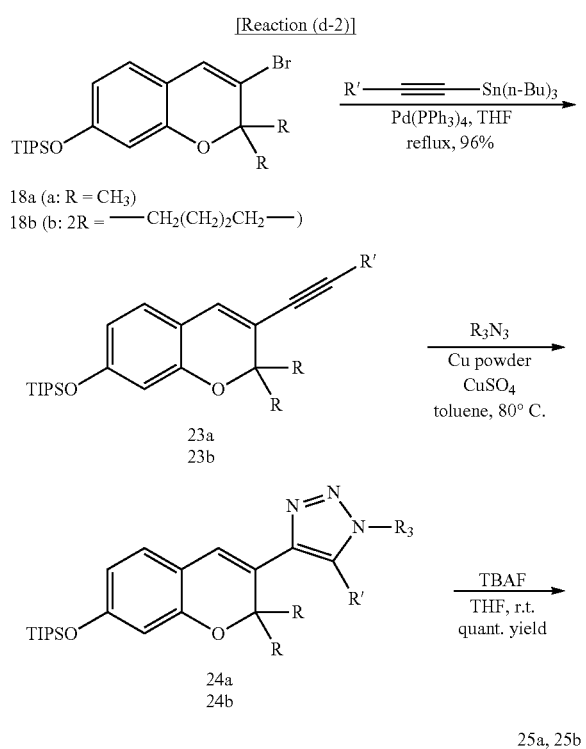

18a (a: R = CH$_3$)
18b (b: 2R = —CH$_2$(CH$_2$)$_2$CH$_2$—)

25a, 25b wherein each of R, R' and R$_3$ is the same as defined in Formula 9. In particular, in the Reaction (d-2), a represents that each R independently is methyl group, and b represents that two of Rs together form —CH$_2$(CH$_2$)$_2$CH$_2$—.

The halogen position of the compound 18a (compound 18b) prepared in Reaction (c) is substituted with an alkynyl group to prepare a compound 23a (compound 23b). Alkynyl tributyltin substituted with R' is used, followed by Sonogashira cross coupling using tetrakis(triphenylphosphine)palladium as a catalyst to obtain the compound 23a (compound 23b).

An azide compound substituted with R$_3$ is added to the compound 23a (compound 23b), followed by click chemistry using copper sulfate as a catalyst to obtain a compound 24a (compound 24b). The compound 24 is treated with TBAF (1.1 to 1.3 equivalent weights) at room temperature for 1 to 2 hours to remove the TIPS protecting groups, resulting in a compound 25a (compound 25b).

Reaction II-3, which is the liquid phase synthesis of the benzopyran compound represented by Formula 10 according to the present invention, comprises the following Reaction (d-3), and will be described in detail as follow.

[Reaction (d-3)]

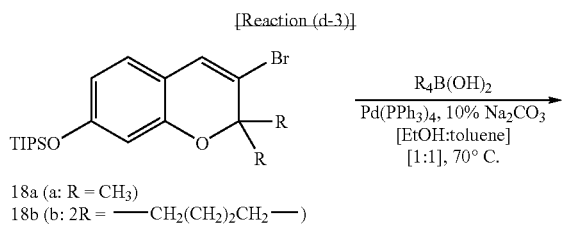

18a (a: R = CH$_3$)
18b (b: 2R = —CH$_2$(CH$_2$)$_2$CH$_2$—)

-continued

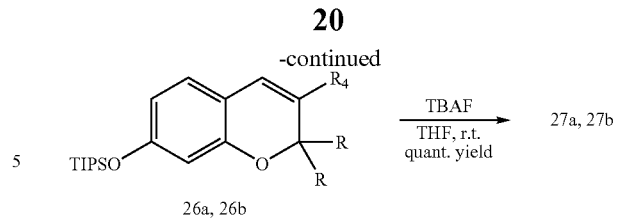

26a, 26b wherein each of R and R$_4$ is the same as defined in Formula 10. In particular, in the Reaction (d-3), a represents that each R independently is methyl group, and b represents that two of Rs together form —CH$_2$(CH$_2$)$_2$CH$_2$—.

The compound 18a (compound 18b) prepared in Reaction (c) is reacted with a boronic acid compound substituted with R$_4$. At this time, a mixed solvent of ethanol and toluene (1:1) is used as a solvent, and tetrakis(triphenylphosphine)palladium is used as a catalyst. 10% sodium carbonate is added, and the reaction is carried out at 70° C., to prepare a compound 26a (compound 26b). TBAF (1.1 to 1.3 equivalent weights) is added thereto, and the reaction is carried out at 0 to 25° C. for 1 to 2 hours to remove the TIPS protecting group. Finally, a compound 27a (compound 27b) can be obtained.

Further, the compound having benzopyran core represented by any one of Formulae 1 to 6 according to the present invention can be prepared by the following solid phase synthesis.

The solid phase synthesis of the compounds with embedded benzopyran motif for core structures according to the present invention may be, but not limited thereto, Reaction III-1, Reaction III-2, or Reaction III-3, comprising three-steps of the following Reactions (e), (f) and (g-1), Reactions (e), (f) and (g-2), and Reactions (e), (f) and (g-3), respectively.

The compound represented by any one of Formulae 1 to 4 can be prepared by Reaction III-1, the compound represented by Formula 5 can be prepared by Reaction III-2, and the compound represented by Formula 6 can be prepared by Reaction III-3.

The solid phase synthesis of the compound represented by any one of Formulae 1 to 6 according to the present invention will be described with reference to the following Reactions (e) to (g-3). However, the scope of the present invention is not limited by these Reactions.

A preparation method of the compounds of the present invention according to the following Reactions (e), (f) and (g-1), Reactions (e), (f) and (g-2), and Reactions (e), (f) and (g-3), comprising the steps of:

Reaction (e) preparing an intermediate compound S through a series of reactions using 2-hydroxyacetophenone substituted with various substituents as a starting material, Reaction (f) preparing a compound S0 by loading the compound S on a polypropylene solid phase support, and then Reaction (g-1) preparing compounds S1, S2, S3, and S4 by reacting the compound S0 with vinyltin and maleimide, and then subjecting to at least one selected from hydrogenation, aromatization and epoxidation;

Reaction (g-2) preparing a compound S5 by reacting the compound S0 with an azide compound; or Reaction (g-3) preparing a compound S6 by reacting the compound S0 with a boronic acid compound.

Each step of the solid phase synthesis of the compound having benzopyran core according to the present invention will be described in detail as follows.

The intermediate compound S of the compound represented by any one of Formulae 1 to 6 according to the present invention is prepared by the pathway represented by the following Reaction (e).

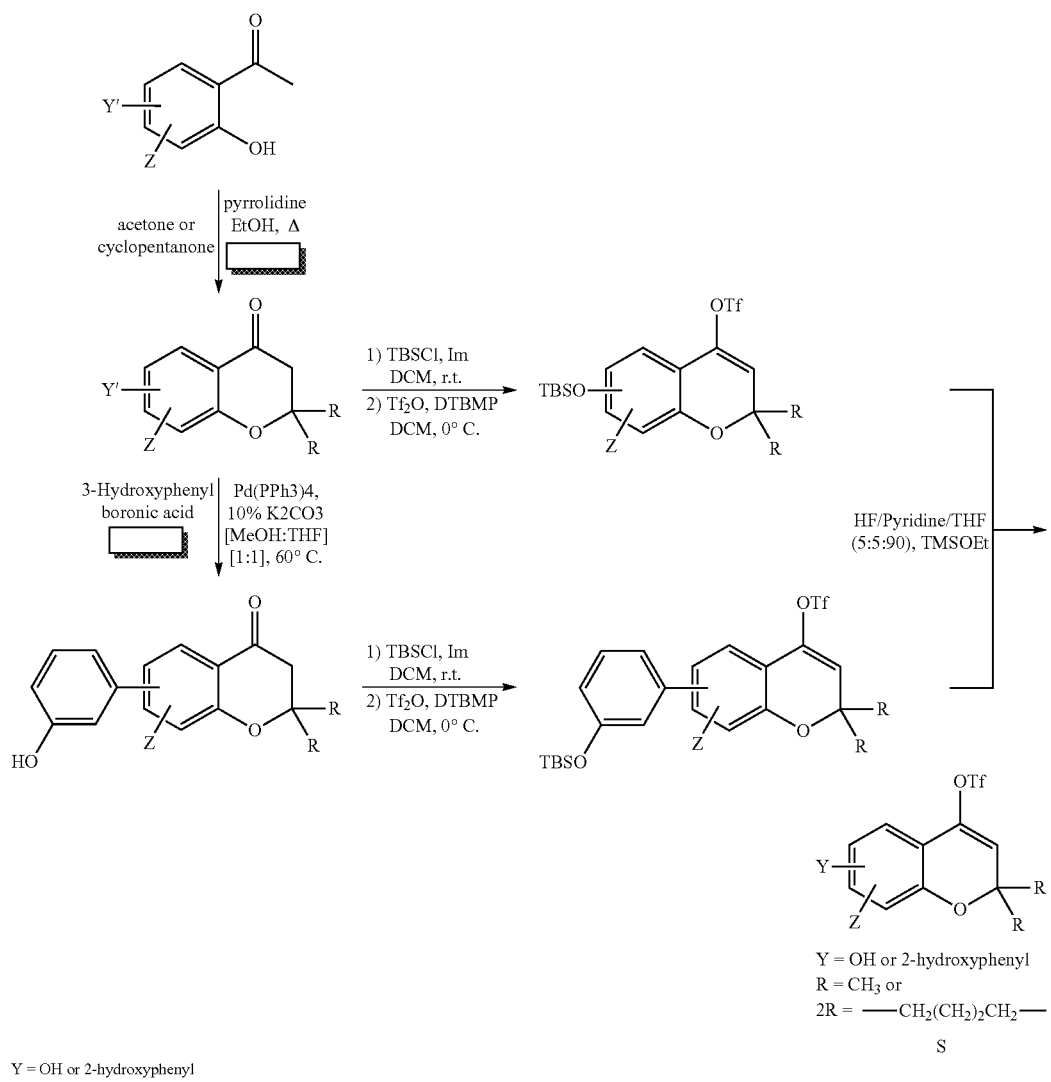

Y = OH or 2-hydroxyphenyl wherein R, Y and Z are the same as defined in Formulae 1 to 6. In particular, in the Reaction (e), each R independently is methyl group, and two of Rs together form —(CH$_2$(CH$_2$)$_2$CH$_2$—.

In Reaction (e), 2-hydroxyacetophenone, in which Z is substituted with different functional groups, can be commercially purchased to be used as a starting material. Acetone (or cyclopentanone, 10 equivalent weights) is added to 2-hydroxyacetophenone, and pyrrolidine (2.0 to 3.0 equivalent weights) that reacts with ketone of acetophenone to form imine and facilitates aldol reactions is used to perform cyclization.

If Y' is bromine, a Suzuki coupling reaction is carried out using 3-hydroxyphenylboronic acid to introduce the phenol group. If Y' is hydroxy group, the above step is omitted. All substrates obtain the hydroxy group through the above step. The prepared hydroxy group of phenol is substituted with a TBS (tert-butyldimethylsilyl) protecting group using TBSCl. (1.1, to 1.5 equivalent weights) at about 0 to 25° C., and vinyl triflate is introduced thereto using trifluorosulfonyl anhydride (1.1 to 1.3 equivalent weights) and DTBMP (1.1 to 1.3 equivalent weights) as a reactant. The prepared compound is treated with hydrogen fluoride/pyridine/THF solution to prepare a compound S.

The intermediate compound S prepared in Reaction (e) is loaded on a solid phase support to prepare a compound S0 by the pathway represented by the following Reaction (f).

[Reaction (f)]

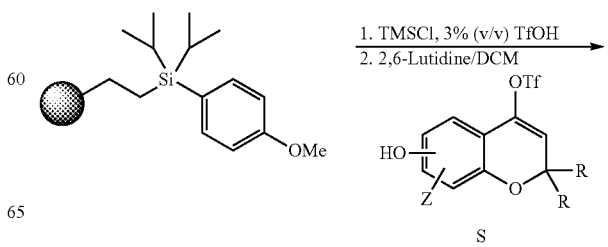

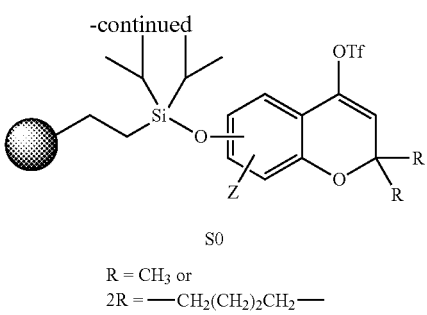

S0

R = CH₃ or
2R = —CH₂(CH₂)₂CH₂— wherein R and Z are the same as defined in Formulae 1 to 6. In particular in the Reaction (f), each R independently is methyl group, and two of Rs together form —CH₂(CH₂)₂CH₂—.

In Reaction (f), a (4-methoxyphenyl)diisopropylsilylpropylpolystyrene (50-100 mesh) resin is commercially purchased to be used as the solid phase support. The compounds prepared in the present invention are stable on solid phase using the resin.

In Reaction (f), the solid phase support is washed with TMSCl (4 equivalent weights) to remove the moisture thereon, and then treated with triflic acid (TfOH, 6 equivalent weights) to be activated. The OTf group of the resin activated as a base is removed from the activated solid phase support, and the solid phase support is treated with 2,6-lutidine (8 equivalent weights) facilitating to attachment of phenol and the compound S (3.0 to 4.0 equivalent weights) to prepare a compound S0, in which the compound S is loaded on the solid phase support.

The solid phase synthesis of the compound having benzopyran core represented by any one of Formulae 1 to 4 according to the present invention can be represented by the following Reaction (g-1), and will be described in detail as follow.

[Reaction (g-1)]

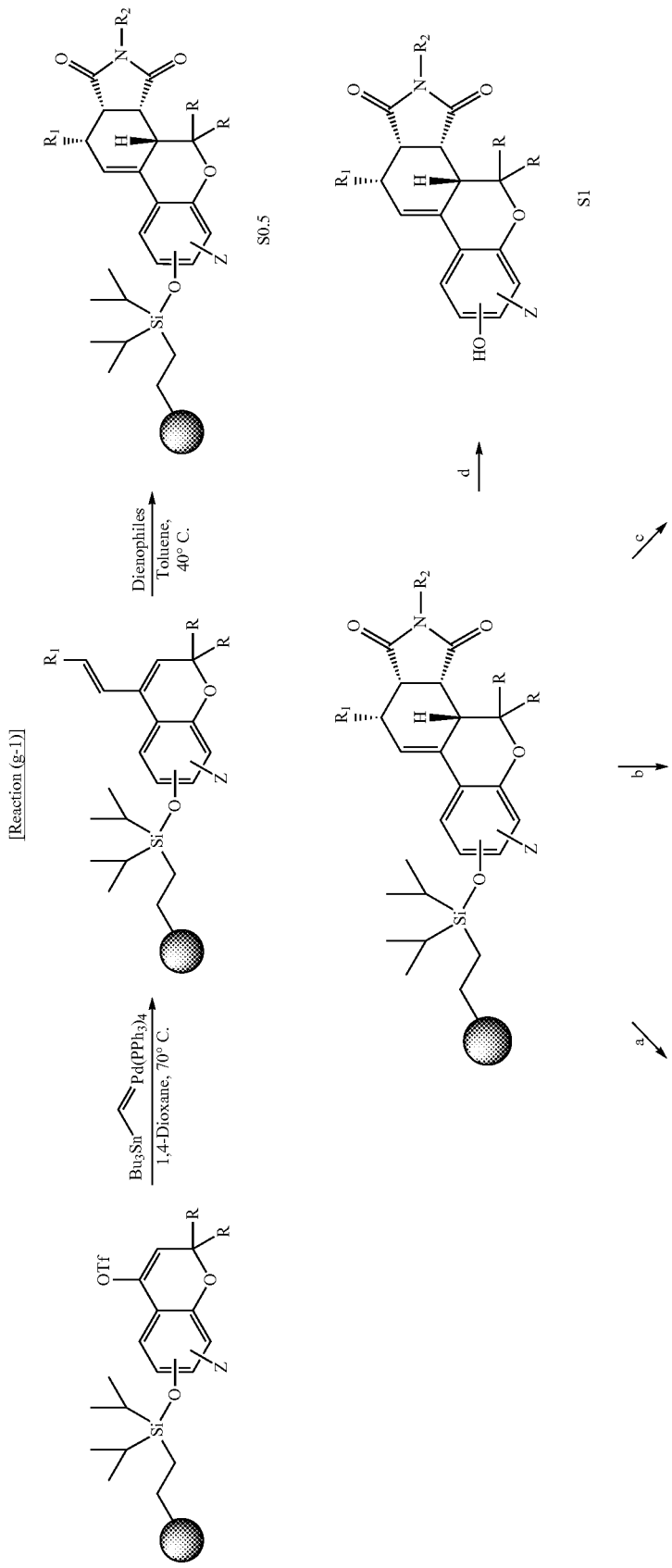

-continued
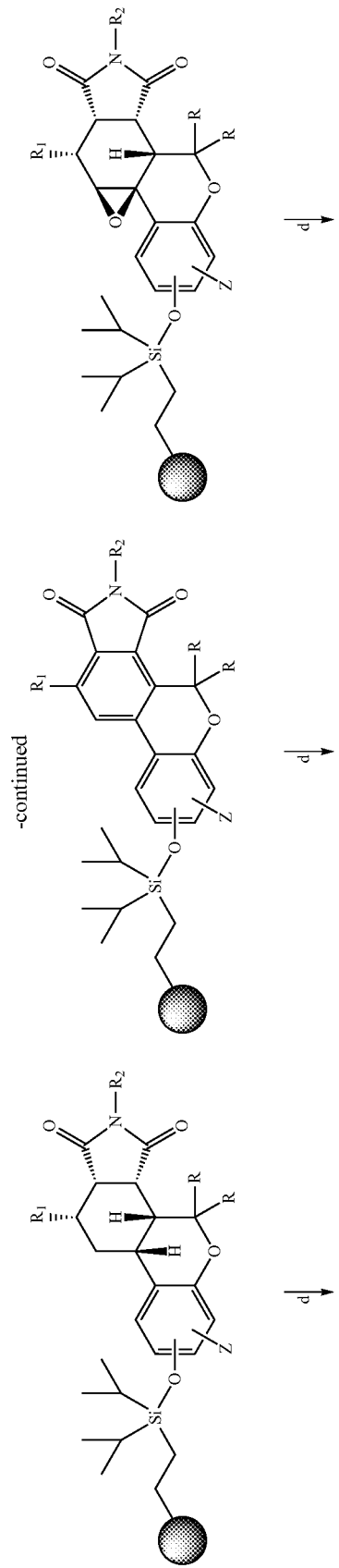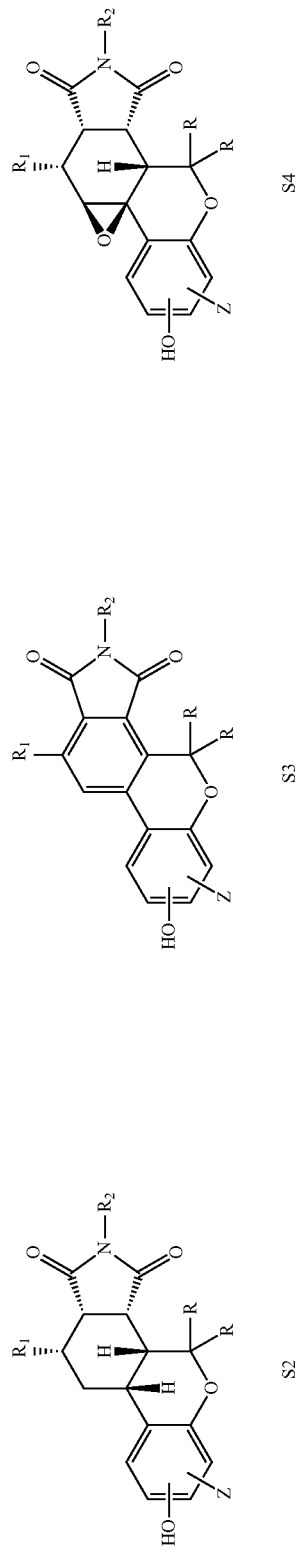
R = CH₃ or
2R = —CH₂(CH₂)₂CH₂—
a: H₂, Pd/C/MeOH, THF
b: DDQ/1,4-Dioxane, 75° C.
c: m-CPBA, DTBMP/DCM, r.t.
d: 1. HF/Pyr/THF
   2. Ethoxytrimethylsilane wherein each of R, $R_1$, $R_2$ and Z is the same as defined in Formulae 1 to 4. In particular, in the Reaction (g-1), each R independently is methyl group, and two of Rs together from —$CH_2(CH_2)_2CH_2$—.

The compound S0 prepared in Reaction (f) is put in a reactor, preferably a 96 well reactor. At, this time, same compounds are put in each row of the well. In each well containing compounds in such way, tributylvinyltin (3.0 equivalent weights) substituted with $R_1$ is added, followed by Stille cross coupling using tetrakis(triphenylphosphine)palladium as a catalyst. At this time, 1,4-dioxane having a high boiling point is used as a solvent, and the reaction is performed in a rotary oven at 70° C. for 24 hours. Maleimide substituted with $R_2$ (3.0 equivalent weights) is added to the compound obtained by the reaction, followed by Diels-Alder Reaction using toluene (1.2 ml) as a solvent. The compound is also reacted in the rotary oven at 40° C. for 24 hours to obtain a compound S0.5. After completing the reaction, the compound is removed from the resin by treating with a solution, in which hydrogen fluoride and pyridine are dissolved in tetrahydrofuran in a volume ration of 5:5:90, and filtered to obtain a desired compound S1.

The compound S0.5 is subjected to hydrogenation using Pd/C as a catalyst while supplying hydrogen gas, and treated with hydrogen fluoride and pyridine to prepare a compound S2.

Further, the compound S0.5 is treated with DDQ (5 equivalent weights), subjected to reaction in the rotary oven at a high temperature of 75□, and then treated with hydrogen fluoride and pyridine to obtain a compound S3.

Finally, the compound S0.5 is treated with m-CPBA as an oxidizing agent, followed by epoxidation, and then treated with hydrogen fluoride and pyridine to obtain a compound S4.

After completing each reaction of the step, each compound is washed with tetrahydrofuran (THF) and dichloromethane (DCM) several times. In particular, in the case of using, palladium for the reaction, the compound is preferably washed with a sodium diethyldithio carbamate trihydrate THF solution to remove palladium impurities.

The solid phase synthesis of the benzopyran compound represented by Formula 5 according to the present invention can be represented by the following Reaction (g-2), and will be described in detail as follow.

[Reaction (g-2)]

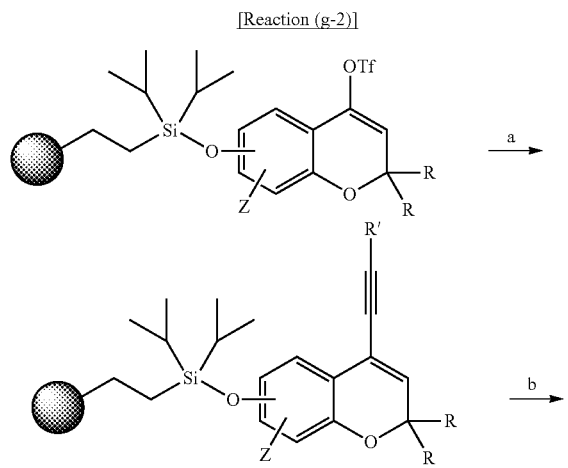

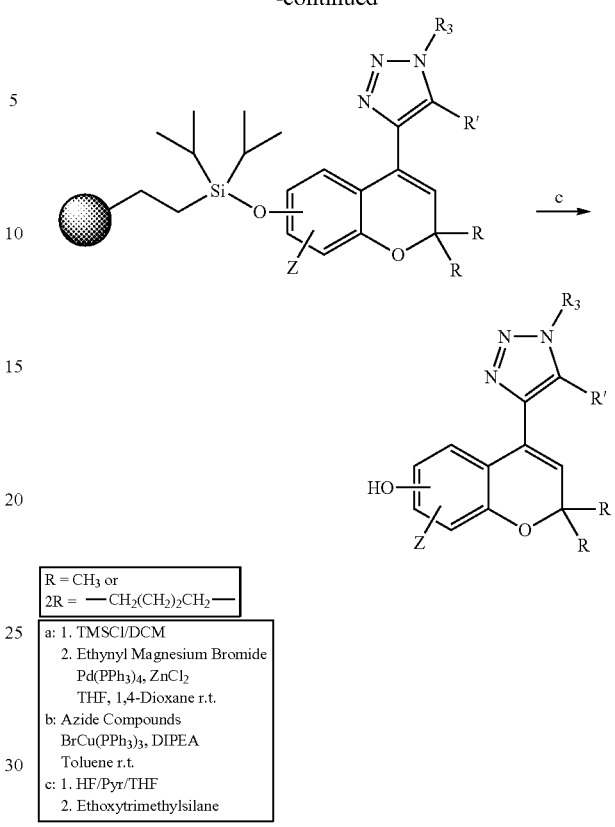

wherein each of R, R', $R_3$ and Z is the same as defined in Formula 5. In particular, in the Reaction (g-2), each R independently is methyl group, and two of Rs together form —$CH_2(CH_2)_2CH_2$—.

The position of the OTf group in the compound S0 prepared in Reaction (f) is substituted with an alkynyl group. Zinc chloride (10 equivalent weights) is added to alkynyl magnesium bromide (8 equivalent weights) that is used to bind the alkynyl group to the compound S0 like a Grignard reagent, so as to substitute magnesium with zinc, followed by Negishi cross coupling using tetrakis(triphenylphosphine) palladium as a catalyst. The intermediate prepared by the Negishi cross coupling is added to the 96 well reactor, in which same compounds are put in each row of the well, in the same manner as in Reaction (g-1). Then, the azide compound substituted with $R_3$ (3 equivalent weights), which is a chemical reagent having dipole, is added to each column, followed by click chemistry using copper sulfate as a catalyst, and then treated with 400 µl of hydrogen fluoride and pyridine to prepare a compound S5.

After completing each reaction in the step, the compound is washed with THF and DCM several times.

The solid phase synthesis of the benzopyran compound represented by Formula 6 according to the present invention can be represented by the following Reaction (g-3), and will be described in detail as follow.

[Reaction (g-3)]

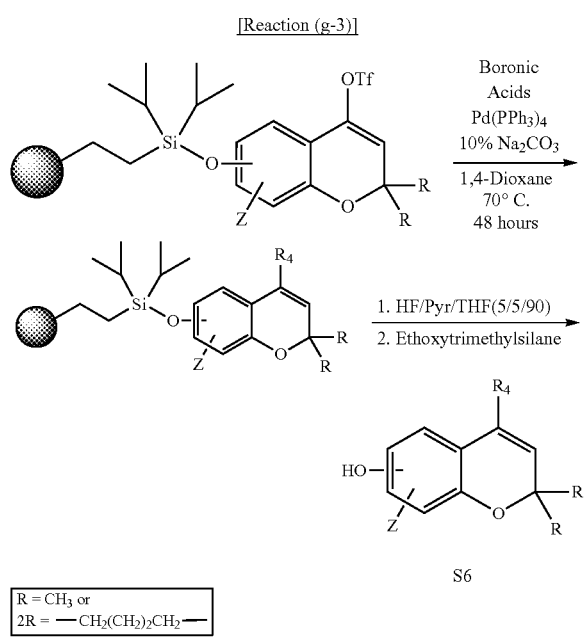

S6

R = CH₃ or
2R = —CH₂(CH₂)₂CH₂— wherein each of R, $R_4$ and Z is the same as defined in Formula 6. In particular, in the Reaction (g-3), each R independently is methyl group, and two of Rs together form —CH₂(CH₂)₂CH₂—.

The compound S0 prepared in Reaction (f) is first put in the 96 well reactor. A boronic acid compound substituted with $R_4$ (3.0 equivalent weights) is put in each column, and subjected to reaction. At this time, 1,4-dioxane is used as a solvent, tetrakis(triphenylphosphine)palladium is used as a catalyst, and 10% sodium carbonate is added. The reaction is preferably performed in a rotary oven at 70□ for 48 hours. Then, the compound is preferably washed with solutions such as THF, DCM, and sodium diethyldithiocarbamate trihydrate, and treated with 400 μl of hydrogen fluoride/pyridine/THF solution to prepare a compound S6.

Further, the compound of the present invention exhibit excellent cytotoxicity against cancer cells, thereby being used as a cancer inhibiting agent, and can be used as an anticancer agent.

Accordingly, the present invention provides an effective anticancer agent comprising the compound having benzopyran core represented by any one of Formulae 1 to 10 as an active ingredient.

Examples of cancer include one or more cancer selected from the group consisting of cervical cancer, lung cancer, pancreatic cancer, non-small cell lung cancer, liver cancer, colon cancer, bone cancer, skin cancer, head or neck cancer, cutaneous or ocular melanoma, uterine cancer, ovarian cancer, rectal cancer, gastric cancer, anal cancer, colon cancer, breast cancer, fallopian tube carcinoma, endometrial carcinoma, vaginal carcinoma, vulvar carcinoma, esophageal cancer, small intestine cancer, endocrine gland cancer, thyroid cancer, parathyroid cancer, adrenal cancer, soft-tissue sarcoma, uterine cancer, penis cancer, prostate cancer, bladder cancer, kidney or hydroureter cancer, renal cell carcinoma, renal pelvic carcinoma, preferably lung cancer, liver cancer, skin cancer or cutaneous melanoma.

Further, the anticancer agent of the present invention may include a nontoxic suitable carrier, excipient, and adjuvant that are conventionally used, in addition to the compound having benzopyran core of the present invention, and may be formulated into the conventional pharmaceutical formulations, for example, oral administrations such as tablets, capsules, troches, liquid, and suspensions, or parenteral formulations.

Further, the dosage of the compound according to the present invention that is administered to human can vary depending on various factors, including patient's age, weight, sex, administration route, health condition, and disease severity. The compound may be administered at a daily dosage of 0.0001 to 1000 mg/kg one time or several times with doctor or pharmacist approval, based on an adult patient. Accordingly, the administration dosage is not intended to limit the scope of the present invention.

The compound of the present invention can be administered to mammals such as rat, mouse, domestic animals and human via various routes. All modes of administration are contemplated, for example, administration can be made orally, rectally or by intravenous, intramuscular, subcutaneous, epidural or intracerebroventricular injection.

EXAMPLES

Hereinafter, the preferred examples will be given for better understanding of the present invention. However, these Examples are for the illustrative purpose only, and the invention is not intended to be limited by these Examples.

Reagent and Apparatus

Starting materials, reactants and solvents were purchased from Sigma-Aldrich Chemical Co., TCI, Acros, fluka, and Maybridge, and used without further purification. A polypropylene solid phase support was purchased from Nova Biochem. ¹H NMR spectra were obtained on Bruker Avance 300 MHz and Varian 500 MHz, and chemical shifts (δ) were recorded in ppm relative to internal standard, TMS. All samples were dissolved in (CDCl₃, DMSO-d₆ and MeOD, unless otherwise mentioned. LC-MS data were recorded with a platform from Thermo Co. For parallel solid phase synthesis, FlexChemSynthesis System was purchased from SciGene (Sunnyvale, Calif.), and used.

Preparation Example 1

Preparation of Compound of Formula 2 [Compound 36 in Table 1] Using Liquid Phase Synthesis (Step 1) Preparation of Compound 2a by Reaction (a)

To a solution of 2,4-dihydroxyacetophenone (3.0 g, 19.72 mmol) and pyrrolidine (3.506 g, 49.29 mmol) dissolved in distilled toluene (100 ml) was added acetone (14.48 ml, 197.18 mmol). Then, the mixture was heated to reflux for 14 hours with a Dean-Stark apparatus. After completing the reaction, the solvent was removed under reduced pressure. The reactant was dissolved with ethylacetate (EA), and washed with 1N hydrochloric acid once, with ammonium chloride twice, and with brine once. The organic layer was dried over anhydrous magnesium sulfate, and filtered. The filtrate was condensed under reduced pressure, and the reaction mixture was purified with a silica gel flash chromatography (EA:hexane=1:4) to give a desired compound as a yellow solid (3.29 g, yield 86.7%); ¹H NMR (CD₃OD, 300 MHz) 7.66 (d, J=8.7, 1H), 6.43 (dd, J=8.6, 2.2, 1H), 6.27 (d, J=2.2, 1H), 2.67 (s, 2H), 1.43 (s, 6H).

(Step 2) Preparation of Compound 3a by Reaction
(a)

A mixture of the compound (1.4 g, 7.28 mmol) prepared in step 1 and imidazole (0.595 g, 8.78 mmol) was stirred in anhydrous dichloromethane (40 ml) under nitrogen. Then, TIPSCl (1.685 g, 6.24 mmol) was added dropwise with a syringe at 0° C., and the mixture was stirred at room temperature for 3 hours. Deionizer water (30 ml) was added thereto, and the reaction mixture was further stirred for 10 minutes. Then, the solvent was removed using ethylacetate, and washed with aqueous ammonium chloride, saturated sodium hydrogen carbonate and brine. The organic layer was dried over anhydrous magnesium sulfate, and filtered. Then, the filtrate was condensed under reduced pressure. The following enol-triflation of reacting ketone with triflic anhydride was directly carried out after the purification with flash column chromatography (EA:Hexane=1:10). To a solution of resulting compound (1.3 g, 3.73 mmol) and DTBMP (0.842 g, 4.10 mmol) in anhydrous dichloromethane at 0° C. with ice bath under nitrogen was added triflic anhydride (1.26 g, 0.753 ml, 4.476 mmol) with a syringe. The mixture was continuously stirred for 10 min at 0° C. The resulting solid was removed through Celite and the filtrate was condensed under reduced pressure. Then, the mixture was dissolved with EA and washed with a saturated $NaHCO_3$ solution and brine. The organic layer was dried over anhydrous magnesium sulfate and filtered. Then, the filtrate was condensed under reduced pressure and the resultant was purified with silica gel flash column chromatography (EA:Hexane=1:50) to give a desired compound (1.56 g, yield 87.0%) as colorless oil; $^1$H-NMR ($CDCl_3$, 300 MHz) 6.87 (d, J=8.4, 1H), 6.28 (dd, J=8.3, 2.3, 1H), 6.15 (d, J=2.2, 1H), 5.25 (s, 1H), 1.28 (s, 6H), 1.05 (m, 3H), 0.87 (d, J=7.0, 18H).

(Step 3) Preparation of Compound 28 by Reaction
(b-1)

To a solution of dissolving the compound (0.729 mmol) prepared in the step 2 and $Pd(PPh_3)_4$ (42.1 mg, 0.0365 mmol) in THF solvent under nitrogen was added Tributylvinyltin (0.875 mmol) with syringe in one portion. The mixture was heated at 70° C., and after 20 hours, the reaction mixture was diluted with diethyl ether (7 ml). The resulting solid was removed through Celite. The filtrate was condensed under reduced pressure, and dissolved in toluene (4 ml). Then, a solution of maleimide reagent (0.875 mmol) in toluene (3 ml) was added to a resulting diene solution at room temperature. After stirring for 10 hours at 40° C., the mixture was filtered through Celite and condensed under reduced pressure. The resultant was purified with silica gel flash column chromatography (EA: Hexane=1:5) to give a desired compound as a white solid (yield 84.1%); $^1$H NMR ($CDCl_3$, 300 MHz) 7.34 (d, J=9.2, 1H), 7.27 (m, 3H), 6.90 (m, 2H), 6.45 (m, 2H), 6.25 (m, 1H), 3.60 (dd, J=8.5, 5.1, 1H), 3.37 (m, 1H), 3.03 (ddd, J=14.9, 7.5, 1.6, 1H), 2.55 (d, J=3.7, 1H), 2.29 (td, J=14.9, 5.5, 1H), 1.88 (s, 3H), 1.33 (s, 3H), 1.23 (m, 3H), 1.07 (d, J=6.2, 18H).

(Step 4) Preparation of Compound 36 by Reaction
(b-1)

A solution of the compound (0.188 mmol) prepared in the step 3 and 10% palladium complex (Pd/C, 10 mol %) in MeOH/THF (1:1, 3 ml) was treated with hydrogen gas at atmospheric pressure. Then, the reaction mixture was stirred for 3 hours at room temperature. After completing the reaction, the reaction mixture was filtered through Celite and the solvent was evaporated under reduced pressure to give a desired compound as a pale brown solid (yield 84.3%); $^1$H NMR ($CDCl_3$, 300 MHz) 7.25 (m, 3H), 6.90 (d, J=8.4, 1H), 6.75 (m, 2H), 6.38 (dd, J=8.4, 2.4, 1H), 6.34 (d, J=2.3, 1H), 3.44 (m, 2H), 3.24 (br s, 1H), 2.46 (m, 1H), 2.16 (m, 2H) 1.992 (m, 1H), 1.73 (s, 3H), 1.51 (m, 1H), 1.42 (s, 3H), 1.19 (m, 3H), 1.06 (d, J=7.1, 18H).

Preparation Example 2

Preparation of Compound of Formula 5 [Compound 57 in Table 1] Using Liquid Phase Synthesis (Step 1) Preparation of Compound 12a by Reaction
(b-2)

First, zinc chloride (2.5 equivalent weights) was dissolved in the distilled THF, and ethynyl magnesium bromide (2 equivalent weights) THF solution was slowly added thereto at 0° C. Then, the mixture was stirred under anhydrous conditions for 30 minutes to prepare a solution A. The compound (0.281 mmol) prepared in the step 2 of Preparation Example 1 was dissolved in THF, and tetrakis(triphenylphosphine) palladium ($Pd(PPh_3)_4$, 5 mol %) was added thereto to prepare a solution B. The solution B was added to the solution A, and then the mixed solution was stirred at 25° C. for 4 hours. The solution was filtered to remove the solid, and the next reaction was directly performed without further purification.

(Step 2) Preparation of Compound 57 by Reaction
(b-2)

A solution of the terminal alkyne compound (0.281 mmol) prepared in the step 1, azide compound (0.561 mmol), copper powder (10 mol %) and $CuSO_4$ (10 mmol %) in toluene (3 ml) was heated overnight at 8000. After completing the reaction, the mixture was filtered through Celite and the filtrate was condensed under reduced pressure. Then, the resultant was purified with silica gel flash column chromatography (EA:Hexane=1:5) to give a desired compound as a pale pink solid (yield 76.1%); $^1$H NMR ($CDCl_3$, 300 MHz) 8.61 (br s, 1H), 7.80 (s, 1H), 7.71 (t, J=7.7, 1H), 7.27 (m, 3H), 6.43 (m, 2H), 6.02 (s, 1H), 5.70 (s, 2H), 1.46 (s, 6H), 1.23 (m, 3H), 1.09 (d, J=7.0, 18H).

Preparation Example 3

Preparation of Compound of Formula 6 [Compound 61 in Table 1] Using Liquid Phase Synthesis
(Reaction (b-3))

To a solution of compound 3a (0.208 mmol) prepared in Preparation Example 1 and $Pd(PPh_3)_4$ (12.0 mg, 0.010 mmol) in a solvent mixture of toluene (1 ml) and ethanol (1 ml) under nitrogen was added a solution of boron reagent (0.229 mmol) and 10% sodium carbonate (0.624 mmol) in a solvent mixture of toluene (1 ml) and ethanol (1 ml). Then, the mixture was heated for 3 hours at 65° C. The resulting solid was removed by filtration through Celite. The filtrate was extracted with ethylacetate and washed with water, saturated $NaHCO_3$ solution, and brine. The organic layer was dried over magnesium sulfate, and filtered. After condensation of the filtrate under reduced pressure, the resultant was purified with silica gel flash column chromatography (EA:Hexane=1:50) to give a desired compound (yield 97.2%) as yellow oil; $^1$H NMR ($CDCl_3$, 300 MHz) 8.23 (s, 1H), 8.21 (d, J=7.5, 1H), 7.68 (d, J=7.7, 1H) 7.55 (t, J=7.7, 1H), 6.73 (d, J=8.4, 1H), 6.48 (d, J=2.4, 1H), 6.38 (dd J=8.4, 2.4, 1H), 5.56 (s, 1H), 1.49 (s, 6H), 1.25 (m, 3H), 1.10 (d, J=7.0, 18H).

Preparation Example 4

Preparation of Compound of Formula 2 [Compound 28 in Table 1] Using Solid Phase Synthesis (Step 1) Preparation of Intermediate Compound S by Reaction (e)

To a solution of 2,4-dihydroxyacetophenone (3.0 g. 19.72 mmol) and pyrrolidine (3.506 g, 49.29 mmol) dissolved in ethanol (100 ml) was added acetone (14.48 ml, 197.18 mmol). Then, the mixture was heated to reflux for 12 hours. After completing the reaction, the solvent was removed under reduced pressure. The reactant was dissolved with EA, and washed with 1N hydrochloric acid once, with ammonium chloride twice, and with brine once. The organic layer was dried over anhydrous magnesium sulfate, and filtered. The filtrate was condensed under reduced pressure, and the reaction mixture was purified with a silica gel flash chromatography (EA:Hexane=1:4) to give a yellow solid (3.08 g, yield 81.3%); $^1$H NMR (CD$_3$OD, 300 MHz) 7.66 (d, J=8.7, 1H), 6.43 (dd, J=8.6, 2.2, 1H), 6.27 (d, J=2.2, 1H), 2.67 (s, 2H), 1.43 (s, 6H).

A mixture of the yellow solid compound (1.4 g, 7.28 mmol) and imidazole (0.595 g, 8.78 mmol) dissolved in anhydrous dichloromethane (40 ml) was stirred under nitrogen. Then, TBSCl (1.323 g, 8.78 mmol) was added dropwise at 0° C. with a syringe, and the mixture was stirred at room temperature for 3 hours. Deionized water (30 ml) was added thereto, and the reaction mixture was further stirred for 10 minutes. Then, the solvent was removed using EA, and washed with aqueous ammonium chloride, saturated sodium hydrogen carbonate and brine. The organic layer was dried over anhydrous magnesium sulfate, and filtered. Then, the filtrate was condensed under reduced pressure. The following, enol-triflation of reacting ketone with triflic anhydride was directly carried out after the purification with flash column chromatography (EA:Hexane=1:10). To a solution of resulting compound (1.3 g, 3.73 mmol) and DTBMP (0.842 g, 4.10 mmol) in anhydrous dichloromethane at 0° C. with ice bath under nitrogen was added triflic anhydride (1.26 g, 0.753 ml, 4.476 mmol) with a syringe. The mixture was continuously stirred for 10 min at 0° C. The resulting solid was removed through Celite and the filtrate was condensed under reduced pressure. Then, the mixture was dissolved with EA and washed with a saturated NaHCO$_3$ solution and brine. The organic layer was dried over anhydrous magnesium sulfate and filtered. Then, the filtrate was condensed under reduced pressure and the resultant was purified with silica gel flash column chromatography (EA:Hexane=1:50) to give a desired compound S (1.56 g, yield 87.0%) as colorless oil; $^1$H-NMR (CDCl$_3$, 300 MHz) 6.87 (d, J=8.4, 1H), 6.28 (dd, J=8.3, 2.3, 1H), 6.15 (d, J=2.2, 1H), 5.25 (s, 1H), 1.28 (s, 6H), 1.05 (m, 3H), 0.87 (d, J=7.0, 18H).

(Step 2) Preparation of Compound S0 by Reaction (f)

Anhydrous dichloromethane (20 ml) was added to (4-methoxyphenyl)diisopropylsilylpropyl polystyrene resin (1.4 g, 1.5 mmol/g, 2.1 mmol) in 50 ml reaction vessel, and shaken and swollen for 15 minutes. TMSCl (912.6 mg, 8.4 mmol) was added to the resin, and subjected to reaction for further 15 minutes to completely remove water. The resin was filtered and washed with 20 ml of dichloromethane three times. Then, the resin was treated with a solution (37.2 ml) of trifluoromethanesulfonic acid (1.89 g, 12.6 mmol) in dichloromethane (3% (v/v)), and subjected to reaction for further 15 minutes to be activated. After the reaction, the resin was filtered, and washed with 20 ml of dichloromethane three times again. Distilled 2,6-lutidine (1.80 g, 16.8 mmol) and the compound S (7.35 mmol) prepared in the step 1 were dissolved in dichloromethane (20 ml) and then applied to the resin. After reaction for 12 hours, the resin was filtered, and washed with 20 ml of dichloromethane three times. The resin was dried under vacuum for 24 hours to give a desired compound S0 (loading level 0.9 mmol/g).

(Step 3) Preparation of Compound 28 by Reaction (g-1)

The compound S0 loaded on resin prepared in the step 2 was loaded on each well of Robbins 96 deep-well filtration block (25 mg/well), and then a solution of tributylvinyltin (21.40 mg, 0.0675 mmol) and tetrakis(triphenylphosphine) palladium (2.6 mg, 0.00225 mmol) in 1,4-dioxane (1.2 ml) was aliquoted in each well of the reaction block. The reaction mixture was shaken in a rotary oven (Robbins Scientific, Sunnyvale, Calif.) at 70° C. for 36 hours. After the reaction, the resin was washed with tetrahydrofuran (THF), dichloromethane (DCM), hexane (HEX) and methanol, sequentially (three times with each solvent). The resin was treated with a solution of 0.2 M diethyldithiocarbamate in THF twice to remove the residual palladiums. N-phenyl maleimide (3 equivalent weights of N-phenyl maleimide (11.69 mg, 0.0675 mmol) in 1.2 ml of toluene) was aliquoted to each well of the reaction block, and the reaction mixture was shaken in a rotary oven (manufactured by Robbins Scientific) at 40° C. for 48 hours. After the reaction, the resin was washed with dimethylformamide (DMF), THF, and DCM, sequentially (three times with each solvent), and dried in a high vacuum desiccator. 0.4 ml of solution (hydrogen fluoride (HF)/pyridine (Pyr)/THF=5/5/90) was added to each well of the reaction block containing the dried resin, and shaken in a rotary oven (manufactured by Robbins Scientific) at 25° C. for 4 hours. 0.8 ml of ethoxytrimethylsilane solution was added to each well to quench the excessive amount of HF, and shaken in a rotary oven (manufactured by Robbins Scientific) for 1 hour. The desired compound S1 was separated from the resin by filtration, and the solution was completely removed using Genevec. The obtained compound was dissolved in a solution of water and acetonitrile (1:1), and then the solution was evaporated using a freeze dryer to give a desired compound as a yellow powder. The yield of the compound S1 was measured using a liquid chromatography/mass spectroscopy (LC/MS) without further purification. (total yield: 71.0%, 5.99 mg) $^1$H NMR (CDCl$_3$, 300 MHz) 7.34 (d, J=9.2, 1H), 7.27 (m, 3H), 6.90 (m, 2H), 6.45 (m, 2H), 6.25 (m, 1H), 3.60 (dd, J=8.5, 5.1, 1H), 3.37 (m, 1H), 3.03 (ddd, J=14.9, 7.5, 1.6, 1H), 2.55 (d, J=3.7, 1H) 2.29 (td, J=14.9, 5.5, 1H), 1.88 (s, 3H), 1.33 (s, 3H).

The compounds of the present invention synthesized by the same method as in the Preparation Example above are summarized in the following Table 1.

TABLE 1

| Compound | Structure | Molecular weight | MS analysis Value (Molecular weight +H⁺) | NMR |
|---|---|---|---|---|
| 2a | 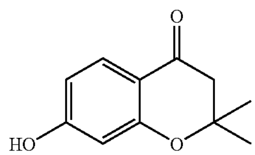 | 192.08 | 193.11 | ¹H NMR (CD₃OD, 300 MHz) 7.66 (d, J = 8.7, 1H), 6.43 (dd, J = 8.6, 2.2, 1H), 6.27 (d, J = 2.2, 1H), 2.67 (s, 2H), 1.43 (s, 6H) |
| 2b | 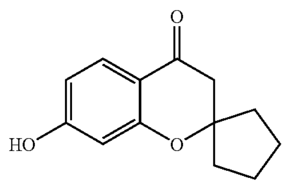 [SMILES: O=C1CC2(CCCC2)Oc2cc(O)ccc21] | 218.09 | 218.83 | ¹H NMR (CDCl₃, 300 MHz) 7.79 (d, J = 8.7, 1H), 7.57 (bs, 1H), 6.52 (dd, J = 8.6, 2.3, 1H), 6.39 (d, J = 2.3, 1H) 2.80 (s, 2H), 2.07 (m, 2H), 1.85 (m, 2H), 1.66 (m, 4H) |
| 3a | 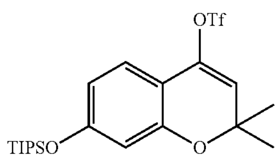 | 480.16 | 481.08 | ¹H NMR (CDCl₃, 300 MHz) 6.87 (d, J = 8.4, 1H), 6.28 (dd, J = 8.3, 2.3, 1H), 6.15 (d, J = 2.2, 1H), 5.25 (s, 1H), 1.28 (s, 6H), 1.05 (m, 3H), 0.87 (d, J = 7.0, 18H) |
| 3b | 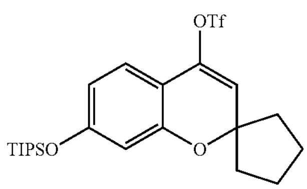 | 506.18 | 507.46 | ¹H NMR (CDCl₃, 300 MHz) 6.87 (d, J = 8.4, 1H), 6.27 (dd, J = 8.3, 2.3, 1H), 6.15 (d, J = 2.2, 1H), 5.35 (s, 1H), 2.14 (m, 2H), 1.84 (m, 2H), 1.63 (m, 4H), 1.22 (m, 3H), 1.06 (d, J = 6.8, 18H) |
| 28 | 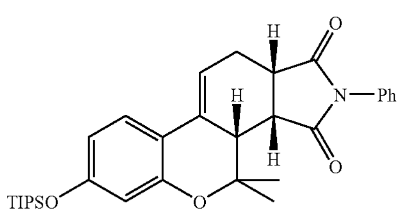 | 554.27 | 555.16 | ¹H NMR (CDCl₃, 300 MHz) 7.34 (d, J = 9.2, 1H), 7.27 (m, 3H), 6.90 (m, 2H), 6.45 (m, 2H), 6.25 (m, 1H), 3.60 (dd, J = 8.5, 5.1, 1H), 3.37 (m, 1H), 3.03 (ddd, J = 14.9, 7.5, 1.6, 1H), 2.55 (d, J = 3.7, 1H), 2.29 (td, J = 14.9, 5.5, 1H), 1.88 (s, 3H), 1.33 (s, 3H), 1.23 (m, 3H), 1.07 (d, J = 6.2, 18H) |
| 29 | 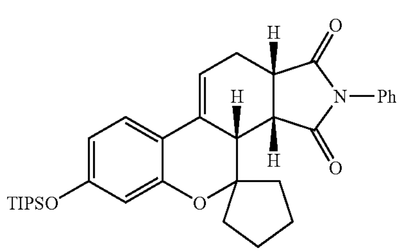 | 557.30 | 558.18 | ¹H NMR (CDCl₃, 300 MHz) 7.31 (m, 1H), 7.24 (m, 3H), 6.90 (m, 2H), 6.48 (m, 1H), 6.45 (m, 1H), 6.24 (br s, 1H), 3.52 (dd,; J = 8.4, 5.7, 1H), 3.36 (t, J = 6.3, 1H), 3.06 (ddd, J = 14.7, 7.6, 1.3, 1H), 2.83 (m, 1H), 2.61 (d, J = 4.6, 1H), 2.27 (td, J = 14.6, 5.0, 1H), 1.72 (m, 8H), 1.23 (m, 3H), 1.08 (d, J = 7.0, 1H) |

TABLE 1-continued

| Compound | Structure | Molecular weight | MS analysis Value (Molecular weight +H$^+$) | NMR |
|---|---|---|---|---|
| 30 | 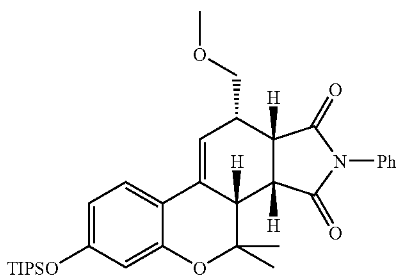 | 575.31 | 576.13 | $^1$H NMR (CDCl$_3$, 300 MHz) 7.36 (d, J = 9.2, 1H), 7.24 (m, 3H), 6.83 (m, 2H), 6.27 (m, 2H), 6.07 (br s, 1H), 4.07 (dd, J = 9.2, 7.0, 1H), 3.91 (t, J = 8.1, 1H), 3.60 (dd, J = 8.3, 5.3, 1H), 3.46 (s, 3H), 3.44 (s, 1H), 2.76 (m, 1H), 2.59 (br s, 1H), 1.89 (s, 3H), 1.30 (s, 3H), 1.22 (m, 3H), 1.08 (d, J = 6.2, 18H) |
| 31 | 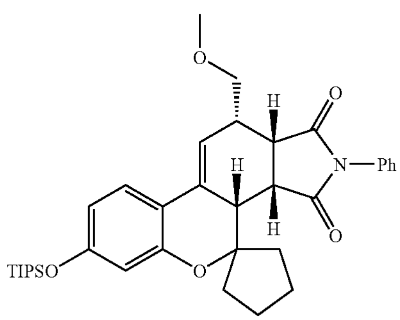 | 601.32 | 602.04 | $^1$H NMR (CDCl$_3$, 300 MHz) 7.35 (m, 1H), 7.24 (m, 3H), 6.83 (m, 2H), 6.46 (m, 2H), 6.06 (dd, J = 4.4, 2.1, 1H), 4.10 (m, 1H), 3.96 (m, 1H), 3.51 (m, 5H), 2.90 (br s, 1H), 2.76 (m, 1H), 2.67 (m, 1H), 1.79 (m, 6H), 1.38 (m, 1H), 1.25 (m, 3H), 1.08 (d, J = 7.0, 18H |
| 32 | 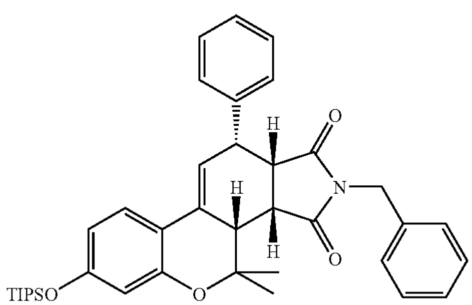 | 621.33 | 622.21 | $^1$H NMR (CDCl$_3$, 300 MHz) 7.30 (m, 5H), 7.08 (m, 6H), 6.50 (m, 2H), 6.32 (br s, 1H), 4.54 (d, J = 14.0, 1H), 4.29 (d, J = 14.0, 1H), 3.72 (t, J = 5.8, 1H), 3.56 (dd, J = 8.0, 4.6, 1H), 3.37 (t, J = 7.4, 1H), 2.68 (br s, 1H), 1.87 (s, 3H), 1.40 (s, 3H), 1.31 (m, 3H), 1.10 (d, J = 6.9, 18H) |
| 33 | 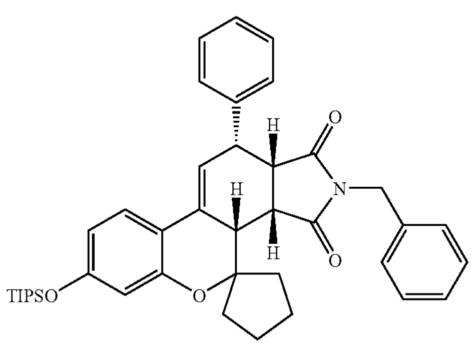 | 647.34 | 648.14 | $^1$H NMR (CDCl$_3$, 300 MHz) 7.31 (m, 8H), 7.07 (m, 3H), 6.52 (m, 1H), 6.48 (m, 1H), 6.37 (br s, 1H), 4.54 (d, J = 14.2, 1H), 4.31 (d, J = 14.1, 1H), 3.73 (t, J = 5.4, 1H), 3.50 (dd, J = 8.0, 5.1, 1H), 3.41 (t, J = 6.4, 1H), 2.74 (br s, 1H), 1.91 (m, 8H), 1.25 (m, 3H), 1.10 (d, J = 6.8, 18H) |

TABLE 1-continued

| Compound | Structure | Molecular weight | MS analysis Value (Molecular weight +H⁺) | NMR |
|---|---|---|---|---|
| 34 | 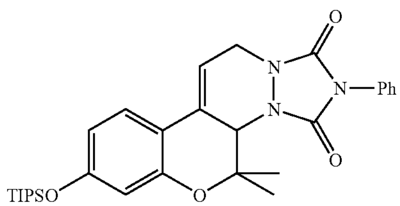 | 533.27 | 534.10 | ¹H NMR (CDCl₃, 300 MHz) 7.52 (m, 4H), 7.40 (m, 1H), 7.26 (s, 1H), 6.50 (dd, J = 8.5, 2.4, 1H), 6.39 (d, J = 2.3, 1H), 6.17 (dd, J = 3.5, 2.1, 1H), 4.87 (s, 1H), 4.55 (ddd, J = 16.4, 5,7, 0.8, 1H), 4.08 (td, J = 16.4, 2.5, 1H), 1.64 (s, 3H), 1.26 (m, 3H), 1.18 (s, 3H), 1.10 (d, J = 6.9, 18H) |
| 35 | 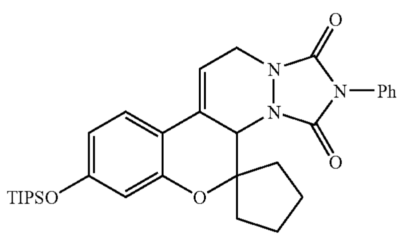 | 559.20 | 560.07 | ¹H NMR (CDCl₃, 300 MHz) 7.51 (m, 4H), 7.38 (m, 1H), 7.23 (m, 1H), 6.49 (dd, J = 8.5, 2.4, 1H), 6.38 (d, J = 2.3, 1H), 6.11 (m, 1H), 5.03 (s, 1H), 4.53 (dd, J = 16.7, 5.5, 1H), 4.12 (td, J = 16.4, 2.4, 1H), 2.31 (m, 1H), 2.02 (m, 2H), 1.66 (m, 5H), 1.25 (m, 3H), 1.10 (d, J = 6.7, 18H) |
| 36 | 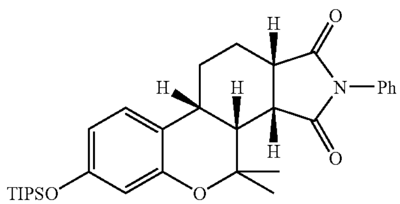 | 533.30 | 534.16 | ¹H NMR (CDCl₃, 300 MHz) 7.25 (m, 3H), 6.90 (d, J = 8.4, 1H), 6.75 (m, 2H), 6.38 (m, J = 8.4, 2.4, 1H), 6.34 (d, J = 2.3, 1H), 3.44 (m, 2H), 3.24 (br s, 1H), 2.46 (m, 1H), 2.16 (m, 2H), 1.92 (m, 1H), 1.73 (s, 3H), 1.51 (m, 1H), 1.42 (s, 3H), 1.19 (m, 3H), 1.06 (d, J = 7.1, 18H) |
| 37 | 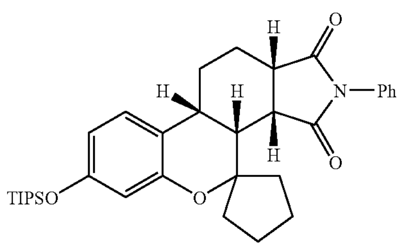 | 559.31 | 560.00 | ¹H NMR (CDCl₃, 300 MHz) 7.25 (m, 3H), 6.88 (d, J = 8.3, 1H), 6.74 (m, 2H), 6.38 (dd, J = 8.4, 2.3, 1H), 6.34 (d, J = 2.3, 1H), 3.35 (dd, J = 9.2, 4.8, 2H), 3.22 (br s, 1H), 2.59 (m, 1H), 2.42 (m, 1H), 2.15 (m, 3H), 1.94 (m, 3H), 1.75 (m, 3H), 1.51 (m, 2H), 1.21 (m, 3H), 1.05 (d, J = 7.1, 18H) |

TABLE 1-continued

| Compound | Structure | Molecular weight | MS analysis Value (Molecular weight +H$^+$) | NMR |
|---|---|---|---|---|
| 38 | 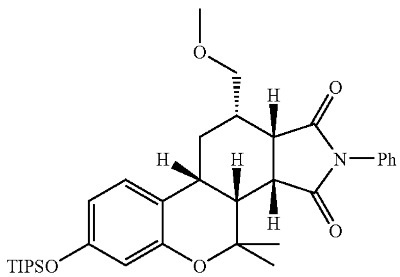 | 600.31 | 601.43 | $^1$H NMR (CDCl$_3$, 300 MHz) 7.25 (m, 3H), 6.89 (d, J = 5.0, 1H), 6.66 (m, 2H), 6.39 (dd, J = 5.0, 1.4, 1H), 6.34 (d, J = 1.4, 1H), 3.85 (dd, J = 5.6, 3.9, 1H), 3.51 (m, 3H), 3.43 (s, 3H), 3.34 (br s, 1H), 2.55 (dd, J = 7.9, 6.9, 1H), 2.39 (m, 1H), 2.19 (dd, J = 4.3, 3.5, 1H), 1.75 (s, 3H), 1.40 (s, 3H), 1.33 (dd, J = 7.9, 6.9, 1H), 1.23 (m, 3H), 1.06 (d, J = 7.1, 18H) |
| 39 | 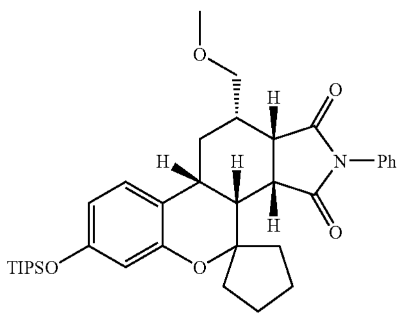 | 603.34 | 604.80 | $^1$H NMR (CDCl$_3$, 300 MHz) 7.24 (m, 3H), 6.87 (d, J = 8.3, 1H), 6.63 (m, 2H), 6.39 (d, J = 8.4, 1H), 3.86 (t, J = 6.9, 1H), 3.53 (t, J = 7.7, 1H), 3.43 (s, 3H), 3.40 (m, 2H), 3.35 (br s, 1H), 2.66 (m, 1H), 2.52 (m, 1H), 2.41 (m, 1H), 2.19 (t, J = 6.3, 1H), 2.08 (m, 1H), 1.98 (m, 1H), 1.82 (m, 1H), 1.71 (m, 4H), 1.48 (m, 1H), 1.20 (m, 3H), 1.07 (d, J = 6.6, 18H) |
| 40 | 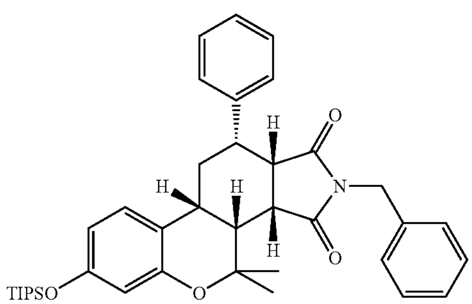 | 623.34 | 624.14 | $^1$H NMR (CDCl$_3$, 300 MHz) 7.23 (m, 7H), 7.08 (m, 3H), 6.71 (m, 2H), 6.52 (m, 2H), 4.54 (d, J = 13.5, 1H), 4.27 (d, J = 13.5, 1H), 3.65 (dd, J = 13.1, 7.8, 1H), 3.40 (dd, J = 8.3, 4.4, 1H), 3.27 (t, J = 8.0, 1H), 2.37 (d, J = 4.3, 1H), 2.26 (d, J = 14.3, 1H), 1.68 (s, 3H), 1.59 (s, 3H), 1.31 (m, 3H), 1.13 (d, J = 6.2, 18H) |
| 41 | 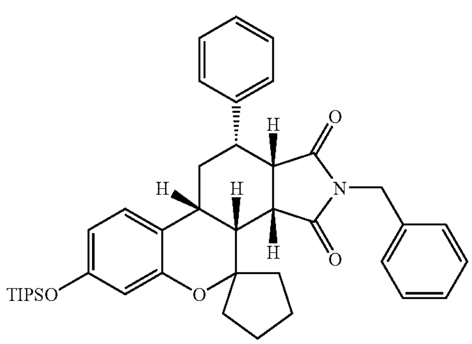 | 649.36 | 650.16 | $^1$H NMR (CDCl$_3$, 300 MHz) 7.22 (m, 6H), 7.04 (m, 4H), 6.89 (d, J = 8.9, 1H), 6.43 (m, 2H), 4.42 (d, J = 13.7, 1H), 4.12 (d, J = 13.7, 1H), 3.41 (m, 2H), 3.27 (m, 1H), 2.52 (m, 2H), 2.29 (dd, J = 7.9, 4.1, 1H), 1.82 (m, 8H), 1.47 (m, 1H), 1.26 (m, 3H), 1.11 (d, J = 7.0, 18H) |

TABLE 1-continued

| Compound | Structure | Molecular weight | MS analysis Value (Molecular weight +H⁺) | NMR |
|---|---|---|---|---|
| 42 | 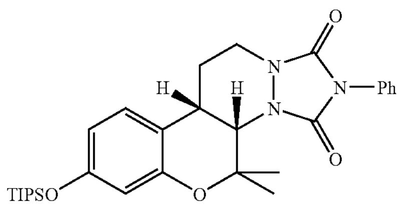 | 535.29 | 536.11 | ¹H NMR (CDCl₃, 300 MHz) 7.50 (m, 4H), 7.38 (t, J = 7.1, 1H), 6.99 (d, J = 8.3, 1H), 6.55 (dd, J = 8.3, 2.3, 1H), 6.43 (d, J = 2.2, 1H), 4.61 (d, J = 6.8, 1H), 4.17 (m, 1H), 3.25 (dt, J = 11.9, 3.2, 1H), 3.12 (m, 1H), 2.27 (m, 1H), 2.12 (m, 1H), 1.46 (d, J = 9.6, 6H), 1.25 (m, 3H). 1.10 (d, J = 7.0, 18H) |
| 43 | 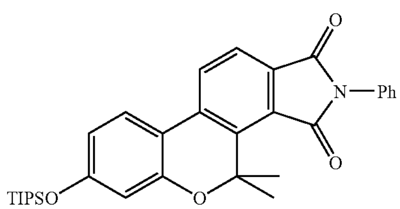 | 527.25 | 528.17 | ¹H NMR (CDCl₃, 300 MHz) 7.97 (d, J = 8.0, 1H), 7.89 (d, J = 7.9, 1H), 7.55 (m, 3H), 7.41 (m, 3H), 6.60 (dd, J = 8.6, 2.4, 1H), 6.44 (d, J = 2.2, 1H), 1.93 (s, 6H), 1.20 (m, 3H). 1.10 (d, J = 7.0, 18H) |
| 44 | 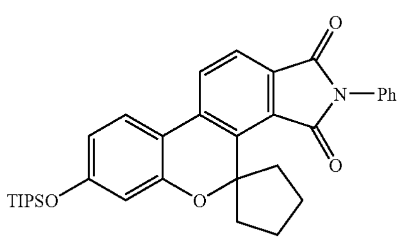 | 553.26 | 554.01 | ¹H NMR (CDCl₃, 300 MHz) 7.95 (4, J = 7.9, 1H), 7.87 (d, J = 7.8, 1H), 7.50 (m, 3H), 7.41 (m, 3H), 6.59 (dd, J = 8.5, 2.2, 1H), 6.47 (d, J = 2.2, 1H), 2.51 (m, 2H), 2.21 (m, 2H), 2.04 (m, 4H), 1.26 (m, 3H), 1.12 (d, J = 7.1, 18H) |
| 45 | 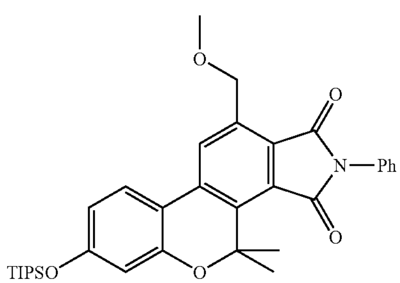 | 571.28 | 572.03 | ¹H NMR (CDCl₃, 300 MHz) 8.12 (s, 1H), 7.54 (m, 6H), 6.61 (td, J = 8.5, 1.7, 1H), 6.50 (d, J = 2.2, 1H), 5.02 (s, 2H), 3.56 (s, 3H), 1.91 (s, 6H), 1.28 (m, 3H), 1.12 (d, J = 7.1, 18H) |
| 46 | 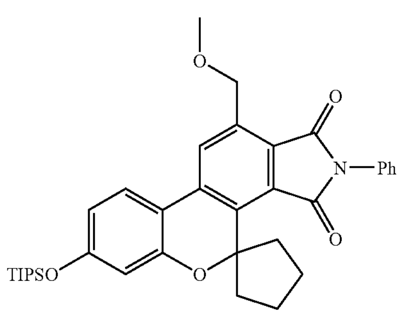 | 597.29 | 598.18 | ¹H NMR (CDCl₃, 300 MHz) 8.11 (s, 1H), 7.52 (m, 4H), 7.38 (m, 2H), 6.60 (d, J = 8.4, 1H), 6.47 (s, 1H), 5.01 (s, 2H), 3.55 (s, 3H), 2.51 (m, 2H), 2.19 (m, 2H), 2.04 (m, 4H), 1.28 (m, 3H), 1.12 (d, J = 7.0. 18H) |

TABLE 1-continued

| Compound | Structure | Molecular weight | MS analysis Value (Molecular weight +H⁺) | NMR |
|---|---|---|---|---|
| 47 | 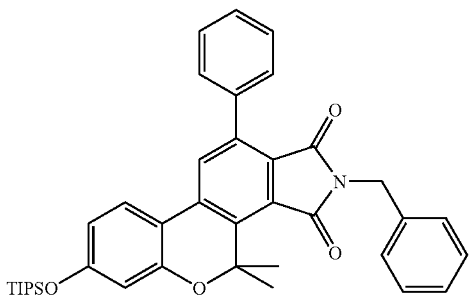 | 617.30 | 618.08 | ¹H NMR (CDCl₃, 300 MHz) 7.75 (s, 1H), 7.50 (m, 6H), 7.41 (m, 2H), 7.29 (m, 3H), 6.56 (dd, J = 8.5, 2.3, 1H), 6.49 (d, J = 2.3, 1H), 4.78 (s, 2H), 1.94 (s, 6H). 1.26 (m, 3H), 1.11 (d, J = 7.1, 18H) |
| 48 | 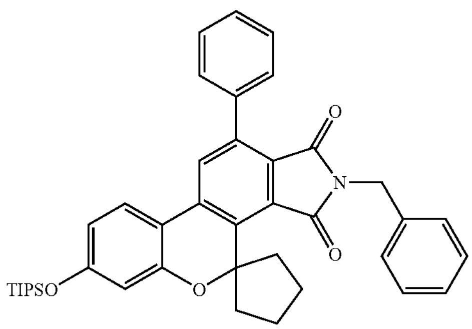 | 643.31 | 644.14 | ¹H NMR (CDCl₃, 300 MHz) 7.68 (s, 1H), 7.42 (m, 6H), 7.32 (m, 2H), 7.21 (m, 3H), 6.48 (dd, J = 8.5, 2.0, 1H), 6.40 (d, J = 2.0, 1H), 4.70 (s, 2H), 2.45 (m, 2H), 2.12 (m, 2H), 2,01 (m, 4H), 1.20 (m, 3H), 1.04 (d, J = 7.1, 18H) |
| 49 | 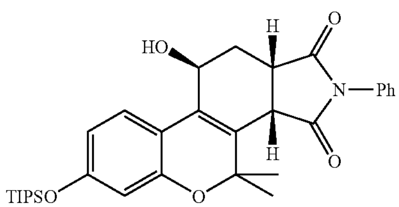 | 547.28 | 548.03 | ¹H NMR (CDCl₃, 300 MHz) 7.44 (m, 3H), 7.27 (m, 2H), 7.20 (d, J = 8.4, 1H), 6.54 (d, J = 2.2, 1H), 6.50 (d, J = 4.1, 1H), 4.96 (s, 1H), 3.91 (d, J = 7.2, 1H), 3.45 (m, 1H), 2.61 (m, 1H), 1.83 (m, 1H), 1.75 (s, 1H), 1.61 (m, 1H), 1.50 (s, 3H), 1.26 (m, 3H), 1.10 (d, J = 7.0, 18H) |
| 50 | 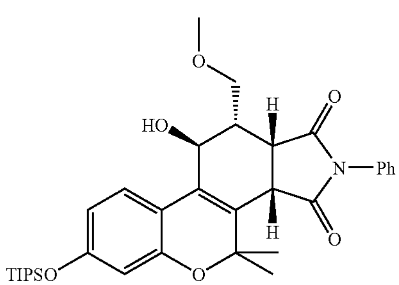 | 591.30 | 592.06 | ¹H NMR (CDCl₃, 300 MHz) 7.47 (m, 2H), 7.41 (m, 1H), 7.33 (m, 2H), 7.22 (m, 1H), 6.51 (dd, J = 8.3, 2.3, 1H), 6.47 (d, J = 2.3, 1H), 4.88 (d, J = 3.4, 1H), 3.85 (d, J = 8.0, 1H), 3.65 (dd, J = 8.0, 5.5, 1H), 3.51 (m, 2H), 3.24 (s, 3H). 2.80 (dd, J = 5.4, 3.5, 1H), 1.80 (s, 3H), 1.62 (m, 1H), 1.47 (s, 3H), 1.25 (m, 3H), 1.10 (d, J = 7.0, 18H) |

TABLE 1-continued

| Compound | Structure | Molecular weight | MS analysis Value (Molecular weight +H+) | NMR |
|---|---|---|---|---|
| 51 | 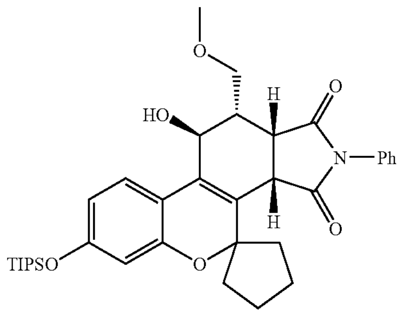 | 617.32 | 618.04 | ¹H NMR (CDCl₃, 300 MHz) 7.47 (m, 2H), 7.38 (m, 1H), 7.31 (m, 2H), 7.22 (m, 1H), 6.51 (dd, J = 8.4, 2.3, 1H), 6.46 (d, J = 2.3, 1H), 4.87 (br s, 1H), 3.87 (d, J = 8.0, 1H), 3.65 (m, 1H), 3.50 (m, 2H), 3.23 (s, 3H), 2.83 (m, 1H), 2.45 (m, 1H), 1.86 (m, 8H), 1.24 (m, 3H), 1.10 (d, J = 7.0, 18H) |
| 52 | 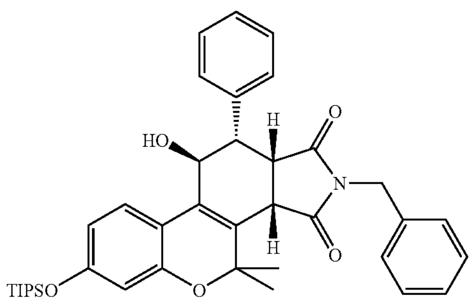 | 637.32 | 638.23 | ¹H NMR (CDCl₃, 300 MHz) 7.19 (m, 4H), 7.12 (m, 7H), 6.49 (m, 2H), 4.98 (br s, 1H), 3.99 (d, J = 14.1, 1H), 3.87 (d, J = 14.1, 1H), 3.76 (m, 1H), 3.65 (m, 2H), 2.00 (s, 1H), 1.71 (s, 1H), 1.67 (s, 1H), 1.24 (m, 3H), 1.10 (d, J = 6.8, 18H) |
| 53 | 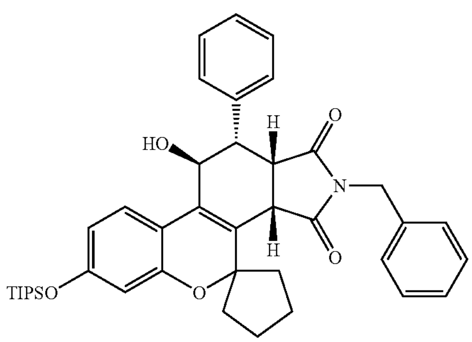 | 663.34 | 664.31 | ¹H NMR (CDCl₃, 300 MHz) 7.19 (m, 4H), 7.10 (m, 7H), 6.50 (m, 2H), 4.97 (d, J = 1.0, 1H), 3.97 (d, J = 14.5, 1H), 3.86 (d, J = 14.0, 1H), 3.76 (m, 1H), 3.66 (m, 2H), 2.26 (m, 2H), 2.11 (m, 2H), 1.94 (m, 3H), 1.83 (m, 2H), 1.25 (m, 3H), 1.11 (d, J = 8.0, 18H) |
| 54 | 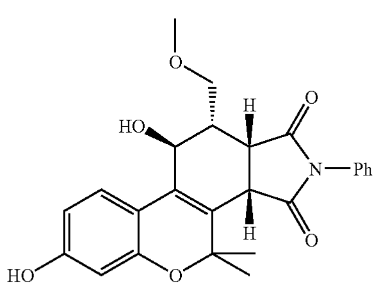 [SMILES: COC[C@@H]1[C@@H]2C(=O)N(c3ccccc3)C(=O)[C@@H]2C2=C(c3ccc(O)cc3OC2(C)C)[C@H]1O] | 435.17 | 434.08 | ¹H NMR (acetone-d₆, 300 MHz) 7.51 (m, 2H), 7.40 (m, 3H), 7.29 (d, J = 8.5, 1H), 6.45 (dd, J = 8.4, 2.4, 1H), 6.36 (d, J = 2.4, 1H), 4.90 (d, J = 2.4, 1H), 3.65 (dd, J = 5.9, 2.2, 1H), 3.43 (m, 2H), 3.21 (s, 3H), 2.77 (m, 1H), 2.06 (m, 2H), 1.75 (s, 3H), 1.50 (s, 3H) |

TABLE 1-continued

| Compound | Structure | Molecular weight | MS analysis Value (Molecular weight +H⁺) | NMR |
| --- | --- | --- | --- | --- |
| 55 | 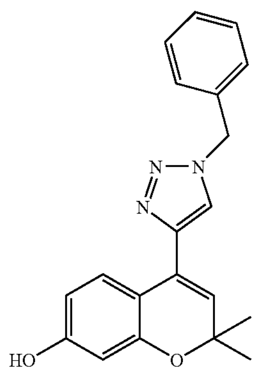 [SMILES: CC1(C)C=C(c2cn(Cc3ccccc3)nn2)c2ccc(O)cc2O1] | 333.15 | 334.42 | ¹H NMR (CDCl₃, 300 MHz) 7.50 (s, 1H), 7.39 (m, 3H), 7.31 (m, 2H), 7.18 (d, J = 8.3, 1H), 6.39 (d, J = 2.2, 1H) 6.37 (dd, J = 8.3, 2.2, 1H), 5.93 (s, 1H), 5.57 (s, 2H), 1.44 (s, 6H) |
| 56 | 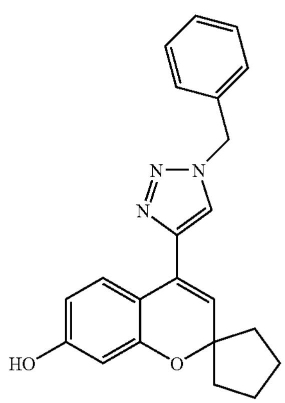 [SMILES: Oc1ccc2c(c1)OC1(C=C2c2cn(Cc3ccccc3)nn2)CCCC1] | 359.16 | 360.30 | ¹H NMR (CDCl₃, 300 MHz) 7.51 (s, 1H), 7.37 (m, 3H), 7.28 (m, 2H), 7.14 (d, J = 8.3, 1H), 6.38 (d, J = 2.2, 1H) 6.33 (dd, J = 8.3, 2.2, 1H), 6.00 (s, 1H), 5.57 (s, 2H), 2.14 (m, 2H), 1.86 (m, 2H), 1.65 (m, 4H) |
| 57 | 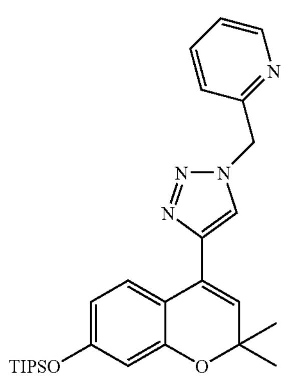 | 490.28 | 490.90 | ¹H NMR (CDCl₃, 300 MHz) 8.61 (br s, 1H), 7.80 (s, 1H), 7.71 (t, J = 7.7, 1H), 7.27 (m, 3H), 6.43 (m, 2H), 6.02 (s, 1H), 5.70 (s, 2H), 1.46 (s, 6H), 1.23 (m, 3H), 1.09 (d, J = 7.0, 18H) |

TABLE 1-continued

| Compound | Structure | Molecular weight | MS analysis Value (Molecular weight +H⁺) | NMR |
|---|---|---|---|---|
| 58 | (pyridin-2-ylmethyl-triazole linked to TIPSO-chromene-spirocyclopentane) | 516.29 | 517.23 | ¹H NMR (CDCl₃, 300 MHz) 8.52 (d, J = 4.4, 1H), 7.71 (s, 1H), 7.62 (t, J = 7.7, 1H), 7.19 (m, 3H), 6.33 (m, 2H), 6.00 (s, 1H), 5.61 (s, 2H), 2.07 (m, 2H), 1.82 (m, 2H), 1.61 (m, 4H), 1.20 (m, 3H), 1.02 (d, J = 7.0, 18H) |
| 59 | (4-(4-methoxyphenyl)-2,2-dimethyl-7-hydroxychromene) | 282.13 | 283.11 | ¹H NMR (CDCl₃, 300 MHz) 7.26 (d, J = 8.6, 2H), 6.91 (d, J = 8.6, 2H), 6.87 (d, J = 8.4, 1H), 6.40 (d, J = 2.2, 1H), 6.31 (dd, J = 8.4, 2.2, 1H), 5.43 (s, 1H), 3.84 (s, 3H), 1.46 (s, 6H) |
| 60 | (4-(4-methoxyphenyl)-7-hydroxychromene-spirocyclopentane) | 308.14 | 309.10 | ¹H NMR (CDCl₃, 300 MHz) 7.29 (d, J = 8.6, 2H), 6.93 (d, J = 8.6, 2H), 6.89 (d, J = 8.5, 1H), 6.40 (d, J = 2.4, 1H), 6.32 (dd, J = 8.3, 2.4, 1H), 5.51 (s, 1H), 3.86 (s, 3H), 2.22 (m, 2H), 1.92 (m, 2H), 1.70 (m, 4H) |
| 61 | (4-(3-nitrophenyl)-2,2-dimethyl-7-TIPSO-chromene) | 453.23 | 454.00 | ¹H NMR (CDCl₃, 300 MHz) 8.23 (s, 1H), 8.21 (d, J = 7.5, 1H), 7.68 (d, J = 7.7, 1H), 7.55 (t, J = 7.7, 1H), 6.73 (d, J = 8.4, 1H), 6.48 (d, J = 2.4, 1H), 6.38 (dd, J = 8.4, 2.4, 1H), 5.56 (s, 1H), 1.49 (s, 6H), 1.25 (m, 3H), 1.10 (d, J = 7.0, 18H) |

TABLE 1-continued

| Compound | Structure | Molecular weight | MS analysis Value (Molecular weight +H⁺) | NMR |
|---|---|---|---|---|
| 62 | (3-nitrophenyl chromene spirocyclopentane with TIPSO) | 479.25 | 480.52 | ¹H NMR (CDCl₃, 300 MHz) 8.23 (s, 1H), 8.21 (d, J = 9.2, 1H), 7.68 (d, J = 7.7, 1H), 7.55 (t, J = 7.7, 1H), 6.73 (d, J = 8.4, 1H), 6.46 (d, J = 2.3, 1H), 6.37 (dd, J = 8.4, 2.3, 1H), 5.61 (s, 1H), 2.21 (m, 2H), 1.93 (m, 2H), 1.70 (m, 4H), 1.27 (m, 3H), 1.10, (d, J = 7.0, 18H) |
| 63 | (thiophene dimethyl chromene with TIPSO) | 414.20 | 415.18 | ¹H NMR (CDCl₃, 300 MHz) 7.29 (d, J = 1.2 1H), 7.21 (d, J = 8.3 1H), 7.10 (m, 2H), 6.48 (d, J = 2.3, 1H), 6.44 (dd, J = 8.3, 2.3, 1H), 5.68 (s, 1H), 1.48 (s, 6H), 1.29 (m, 3H), 1.12 (d, J = 7.0, 18H) |
| 64 | (thiophene chromene spirocyclopentane with TIPSO) | 440.22 | 441.16 | ¹H NMR (CDCl₃, 300 MHz) 7.27 (s, 1H), 7.19 (d, J = 8.1, 1H), 7.01 (m, 2H), 6.41 (m, 2H), 5.73 (s, 1H), 2.17 (m, 2H), 1.90 (m, 2H), 1.67 (m, 4H), 1.26 (m, 3H), 1.11 (d, J = 7.0, 18H) |
| 65 | (pyridyl dimethyl chromene with TIPSO) | 409.24 | 410.20 | ¹H NMR (CDCl₃, 300 MHz) 8.60 (d, J = 1.7, 1H), 8.58 (d, J = 1.5, 1H), 7.66 (dt, J = 7.8, 1.7, 1H), 7.31 (dd, J = 7.9, 4.9, 1H), 6.76 (d, J = 8.4, 1H), 6.47 (d, J = 2.4, 1H), 6.37 (dd, J = 8.4, 2.4, 1H), 5.51 (s, 1H), 1.49 (s, 6H), 1.25 (m, 3H), 1.10 (d, J = 7.0, 18H) |
| 66 | (pyridyl chromene spirocyclopentane with TIPSO) | 435.26 | 436.31 | ¹H NMR (CDCl₃, 300 MHz) 8.60 (m, 2H), 7.67 (dt, J = 7.8, 1.7, 1H), 7.32 (dd, J = 7.9, 4.9, 1H), 6.76 (d, J = 8.4, 1H), 6.45 (d, J = 2.4, 1H), 6.36 (dd, J = 8.4, 2.4, 1H), 5.59 (s, 1H), 2.19 (m, 2H), 1.92 (m, 2H), 1.71 (m, 4H), 1.27 (m, 3H), 1.10 (d, J = 7.0, 18H) |

TABLE 1-continued

| Compound | Structure | Molecular weight | MS analysis Value (Molecular weight +H⁺) | NMR |
|---|---|---|---|---|
| 67 | 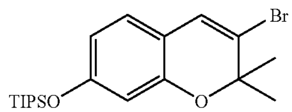 | 410.13 | 410.97 | ¹H NMR (CDCl₃, 300 MHz) 6.80 (d, J = 8.1, 1H), 6.70 (s, 1H), 6.43 (dd, J = 8.2, 2.2, 1H), 6.39 (d, J = 1.8, 1H), 1.55 (s, 6H), 1.27 (m, 3H), 1.12 (d, J = 7.0, 18H) |
| 68 | 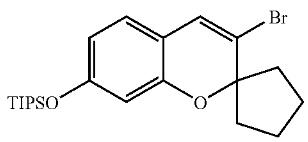 | 436.14 | 437.28 | ¹H NMR (CDCl₃, 300 MHz) 6.79 (d, J = 8.2, 1H), 6.70 (s, 1H), 6.42 (dd, J = 8.1, 2.3, 1H), 6.36 (d, J = 8.2, 2.1, 1H), 2.09 (m, 4H), 1.90 (m, 2H), 1.73 (m, 2H), 1.26 (m, 3H), 1.10 (d, J = 7.0, 18H) |
| 69 | 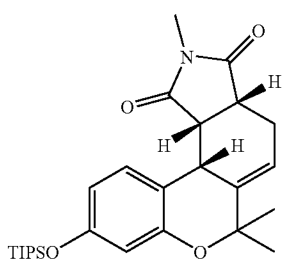 | 469.3 | 470.5 | ¹H NMR (CDCl₃, 600 MHz) 7.15 (d, J = 8.3, 1H), 6.59 (dd, J = 8.3, 2.3, 1H), 6.46 (d, J = 2.3, 1H), 5.82 (m, 1H), 3.54 (d, J = 6.2, 1H), 3.45 (dd, J = 8.6, 6.5, 1H), 3.21 (t, J = 7.7, 1H), 2.87 (m, 1H), 2.83 (s, 3H), 2.21 (m, 1H), 1.35 (s, 3H), 1.31 (s, 3H), 1.26 (m, 3H), 1.12 (d, J = 7.0, 18H) |
| 70 | 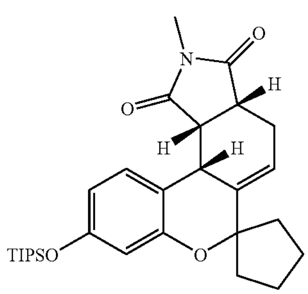 | 495.28 | 496.28 | ¹H NMR (CDCl₃, 300 MHz) 7.16 (d, J = 8.3, 1H), 6.59 (dd, J = 8.3, 2.3, 1H), 6.45 (d, J = 2.3, 1H), 5.84 (m, 1H), 3.54 (d, J = 5.9, 1H), 3.47 (dd, J = 8.5, 6.3, 1H), 3.22 (t, J = 7.5, 1H), 2.88 (m, 1H), 2.83 (s, 3H), 2.21 (m, 1H), 1.83 (m, 4H), 1.63 (m, 4H), 1.25 (m, 3H), 1.10 (d, J = 7.0, 18H) |
| 71 | 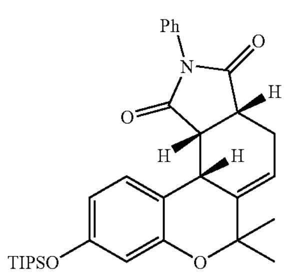 | 531.28 | 532.17 | ¹H NMR (CDCl₃, 300 MHz) 7.36 (m, 3H), 7.15 (m, 3H), 6.58 (dd, J = 8.3, 2.5, 1H), 6,45 (d, J = 2.4, 1H), 5.92 (m, 1H), 3.60 (m, 2H), 3.38 (t, J = 6.9, 1H), 2.97 (ddd, J = 13.5, 7.5, 1.5, 1H), 2.31 (m, 1H), 1.84 (m, 4H), 1.32 (s, 1H), 1.23 (m, 3H), 1.10 (d, J = 7.0, 18H) |

TABLE 1-continued

| Compound | Structure | Molecular weight | MS analysis Value (Molecular weight +H⁺) | NMR |
|---|---|---|---|---|
| 72 | 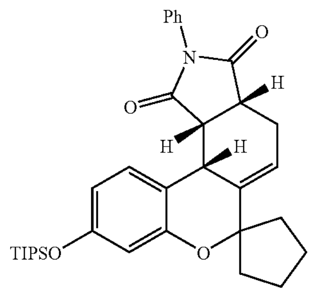 | 557.30 | 558.21 | ¹H NMR (CDCl₃, 300 MHz) 7.37 (m, 3H), 7.15 (m, 3H), 6.58 (dd, J = 8.3, 2.5, 1H), 6.43 (d, J = 2.4, 1H), 5.95 (m, 1H), 3.60 (m, 2H), 3.40 (t, J = 6.9, 1H), 2.97 (ddd, J = 13.5, 7.5, 1.5, 1H), 2.25 (m, 1H), 1.82 (s, 4H), 1.67 (m, 4H), 1.25 (m, 3H), 1.08 (d, J = 7.0, 18H) |
| 73 | 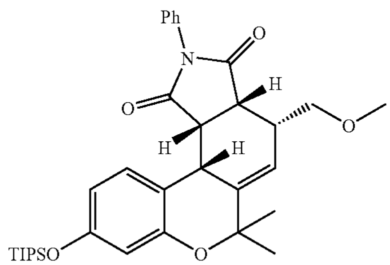 | 575.31 | 576.88 | ¹H NMR (CDCl₃, 300 MHz) 7.32 (m, 3H), 7.14 (m, 3H), 6.59 (dd, J = 8.3, 2.5, 1H), 6.45 (d, J = 2.4, 1H), 5.77 (s, 1H), 4.04 (m, 1H), 3.87 (t, J = 8.8, 1H), 3.64 (br s, 1H), 3.55 (m, 1H), 3.45 (s, 4H), 2.70 (br s, 1H), 1.45 (s, 3H), 1.31 (s, 3H), 1.20 (m, 3H), 1.08 (d, J = 7.0, 18H) |
| 74 | 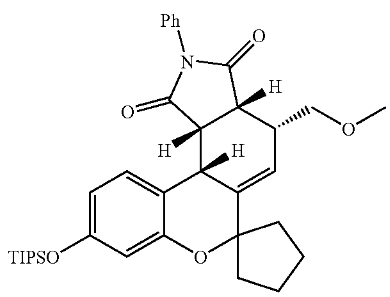 | 601.32 | 602.17 | ¹H NMR (CDCl₃, 300 MHz) 7.37 (m, 3H), 7.17 (d, J = 8.3, 1H), 7.11 (d, J = 7.4, 2H), 6.58 (dd, J = 8.3, 2.5, 1H), 6.44 (d, J = 2.4, 1H), 5.79 (t, J = 3.1, 1H), 4.05 (dd, J = 9.2, 7.1, 1H), 3.87 (t, J = 8.8, 1H), 3.66 (br s, 1H), 3.57 (m, 1H), 3.48 (s, 4H), 2.70 (br s, 1H), 1.86 (m, 4H), 1.64 (m, 2H), 1.56 (m, 2H), 1.25 (m, 3H), 1.08 (d, J = 7.0, 18H) |
| 75 | 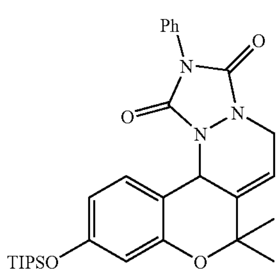 | 533.27 | 534.95 | ¹H NMR (CDCl₃, 300 MHz) 7.63 (d, J = 7.8, 2H), 7.52 (t, J = 7.4, 2H), 7.41 (t, J = 7.4, 1H), 6.92 (d, J = 8.4, 1H), 6.47 (dd, J = 8.4, 2.3, 1H), 6.42 (d, J = 2.2, 1H), 5.80 (m, 1H), 5.69 (s, 1H), 4.30 (dd, J = 16.3, 4.4, 1H), 4.08 (dt, J = 16.3, 2.3, 1H), 1.59 (s, 3H), 1.57 (s, 3H), 1.23 (m, 3H), 1.08 (d, J = 7.0, 18H) |

TABLE 1-continued

| Compound | Structure | Molecular weight | MS analysis Value (Molecular weight +H⁺) | NMR |
|---|---|---|---|---|
| 76 | 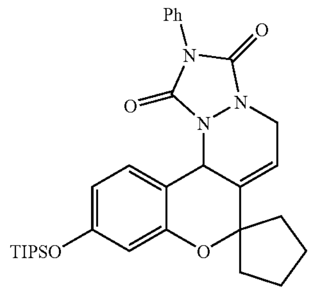 | 559.29 | 560.98 | ¹H NMR (CDCl₃, 300 MHz) 7.62 (d, J = 7.7, 2H), 7.52 (t, J = 7.3, 2H), 7.41 (t, J = 7.3, 1H), 7.07 (d, J = 8.5, 1H), 6.44 (dd, J = 8.5, 2.3, 1H), 6.36 (d, J = 2.2, 1H), 5.90 (m, 1H), 5.76 (s, 1H), 4.32 (dd, J = 16.4, 4.6, 1H), 4.07 (dt, J = 16.4, 2.3, 1H), 2.22 (m, 1H), 2.03 (m, 4H), 1.80 (m, 3H), 1.23 (m, 3H), 1.08 (d, J = 7.0, 18H) |
| 77 | 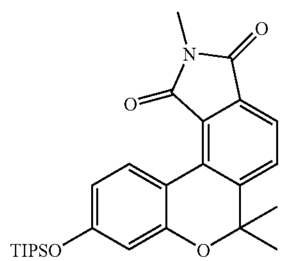 | 465.23 | 466.00 | ¹H NMR (CDCl₃, 300 MHz) 8.49 (d, J = 8.7, 1H), 7.64 (d, J = 7.7, 1H), 7.47 (d, J = 7.6, 1H), 6.60 (dd, J = 8.8, 2.5, 1H), 6.41 (d, J = 2.5, 1H), 3.12 (s, 3H), 1.55 (s, 6H), 1.23 (m, 3H), 1.05 (d, J = 7.0, 18H) |
| 78 | 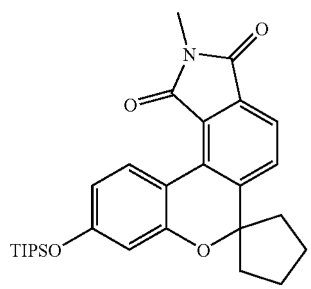 | 491.25 | 492.19 | ¹H NMR (CDCl₃, 300 MHz) 8.52 (d, J = 8.8, 1H), 7.70 (d, J = 7.7, 1H), 7.54 (d, J = 7.7, 1H), 6.66 (dd, J = 8.8, 2.5, 1H), 6.51 (d, J = 2.4, 1H), 3.19 (s, 3H), 2.21 (m, 2H), 1.89 (m, 6H), 1.30 (m, 3H), 1.11 (d, J = 7.0, 18H) |
| 79 | 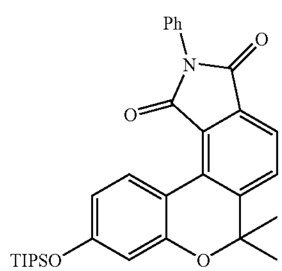 | 527.25 | 528.00 | ¹H NMR (CDCl₃, 300 MHz) 8.56 (d, J = 8.8, 1H), 7.83 (d, J = 7.7, 1H), 7.62 (d, J = 7.7, 1H), 7.49 (m, 5H), 6.63 (dd, J = 8.8, 2.4, 1H), 6.54 (d, J = 2.4, 1H), 1.65 (s, 6H), 1.27 (m, 3H), 1.11 (d, J = 7.0, 18H) |
| 80 | 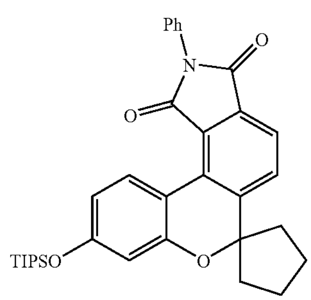 | 553.26 | 554.19 | ¹H NMR (CDCl₃, 300 MHz) 8.53 (d, J = 8.7, 1H), 7.81 (d, J = 7.5, 1H), 7.62 (d, J = 7.5, 1H), 7.48 (m, 5H), 6.63 (dd, J = 8.5, 2.3, 1H), 6.53 (d, J = 2.3, 1H), 2.24 (m, 2H), 1.92 (m, 6H), 1.26 (m, 3H), 1.11 (d, J = 7.0, 18H) |

TABLE 1-continued

| Compound | Structure | Molecular weight | MS analysis Value (Molecular weight +H⁺) | NMR |
|---|---|---|---|---|
| 81 | 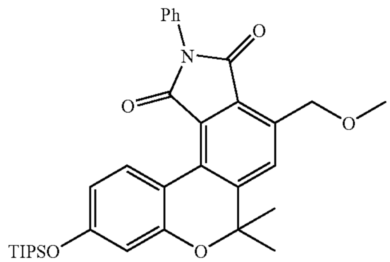 | 571.28 | 572.24 | ¹H NMR (CDCl₃, 300 MHz) 8.48 (d, J = 8.8, 1H), 7.77 (s, 1H), 7.42 (m, 5H), 6.61 (dd, J = 8.8, 2.4, 1H), 6.54 (d, J = 2.4, 1H), 5.03 (s, 2H), 3.55 (s, 3H), 1.65 (s, 6H). 1.27 (m, 3H), 1.11 (d, J = 7.0, 18H) |
| 82 | 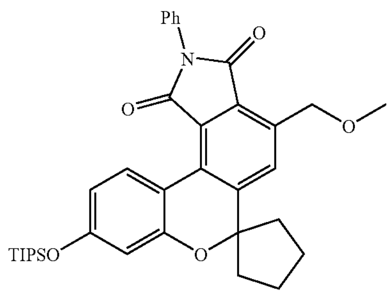 | 597.29 | 598.17 | ¹H NMR (CDCl₃, 300 MHz) 8.45 (d, J = 8.8, 1H), 7.78 (s, 1H), 7.45 (m, 5H), 6.61 (dd, J = 8.7, 2.1, 1H), 6.52 (d, J = 2.0, 1H), 5.03 (s, 2H), 3.56 (s, 3H), 2.24 (m, 2H), 1.94 (m, 6H), 1.28 (m, 3H), 1.11 (d, J = 7.1, 18H) |
| 83 | 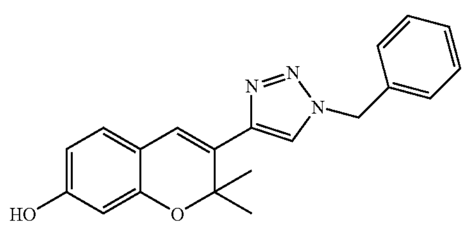 [SMILES: CC1(C)Oc2cc(O)ccc2C=C1c1cn(Cc2ccccc2)nn1] | 333.15 | 334.42 | ¹H NMR (CDCl₃, 300 MHz) 7.43 (s, 1H), 7.40 (m, 3H), 7.30 (m, 2H), 6.86 (d, J = 8.8, 1H), 6.58 (s, 1H), 6.34 (m, 2H), 5.53 (s, 2H), 1.65 (s, 6H) |
| 84 | 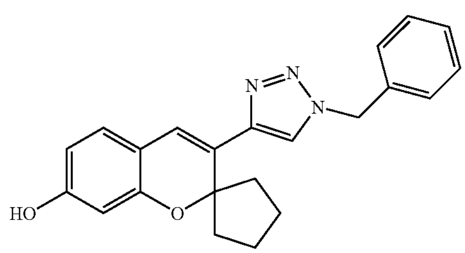 [SMILES: Oc1ccc2c(c1)OC1(CCCC1)C(c1cn(Cc3ccccc3)nn1)=C2] | 359.16 | 360.30 | ¹H NMR (CDCl₃, 300 MHz) 7.39 (d, J = 9.2, 3H), 7.29 (m, 2H), 6.84 (d, J = 7.9, 1H), 6.63 (s, 1H), 6.36 (d, J = 2.2, 1H), 6.33 (s, 1H), 5.52 (s, 2H), 2.14 (m, 4H), 1.90 (m, 2H), 1.76 (m, 2H) |
| 85 | 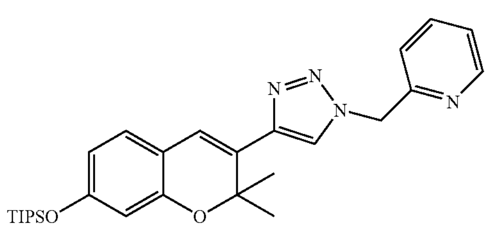 | 490.28 | 491.32 | ¹H NMR (CDCl₃, 300 MHz) 8.62 (d, J = 4.8, 1H), 7.72 (m, 2H), 7.28 (m, 2H), 6.87 (d, J = 8.8, 1H), 6.64 (s, 1H), 6.41 (m, 2H), 5.66 (s, 2H), 1.66 (s, 6H), 1.25 (m, 3H), 1.11 (d, J = 7.0, 18H) |

TABLE 1-continued

| Compound | Structure | Molecular weight | MS analysis Value (Molecular weight +H⁺) | NMR |
|---|---|---|---|---|
| 86 | (chromene with TIPSO, spirocyclopentane, and triazole-CH2-pyridine substituent) | 516.29 | 517.55 | ¹H NMR (CDCl₃, 300 MHz) 8.62 (d, J = 4.4, 1H), 7.71 (m, 2H), 7.24 (m, 2H), 6.87 (d, J = 8.0, 1H), 6.71 (s, 1H), 6.40 (m, 2H), 5.66 (s, 2H), 2.17 (m, 4H), 1.94 (m, 2H), 1.79 (m, 2H), 1.26 (m, 3H), 1.10 (d, J = 7.0, 18H) |
| 87 | (chromene with HO, gem-dimethyl, 4-methoxyphenyl substituent) | 282.13 | 283.09 | ¹H NMR (CDCl₃, 300 MHz) 7.22 (d, J = 8.7, 2H), 6.88 (m, 3H), 6.37 (m, 2H), 6.19 (s, 1H), 4.84 (br s, 1H), 3.82 (s, 3H), 1.50 (s, 2H) |
| 88 | (chromene with TIPSO, spirocyclopentane, 4-methoxyphenyl substituent) | 464.27 | 465.09 | ¹H NMR (CDCl₃, 300 MHz) 7.23 (d, J = 8.7, 2H), 6.89 (m, 3H), 6.46 (m, 2H), 6.33 (s, 1H), 3.84 (s, 3H), 2.18 (m, 2H), 1.91 (m, 4H), 1.67 (m, 2H), 1.28 (m, 3H), 1.12 (d, J = 7.0, 18H) |
| 89 | (chromene with TIPSO, gem-dimethyl, 3-nitrophenyl substituent) | 453.23 | 454.06 | ¹H NMR (CDCl₃, 300 MHz) 8.15 (dt, J = 8.3, 1.1, 2H), 7.63 (dt, J = 6.1, 1.1, 1H), 7.53 (td, J = 7.7, 0.8, 1H), 6.93 (d, J = 7.7, 1H), 6.48 (d, J = 2.3, 1H), 6.44 (s, 1H), 6.38 (s, 1H), 1.54 (s, 6H), 1.25 (m, 3H), 1.11 (d, J = 7.0, 18H) |
| 90 | (chromene with TIPSO, spirocyclopentane, 3-nitrophenyl substituent) | 479.25 | 480.05 | ¹H NMR (CDCl₃, 300 MHz) 8.14 (dt, J = 8.3, 1.1, 2H), 7.61 (dt, J = 6.1, 1.1, 1H), 7.50 (td, J = 7.7, 0.8, 1H), 6.93 (d, J = 7.7, 1H), 6.47 (d, J = 2.3, 1H), 6.43 (s, 2H), 2.23 (m, 2H), 1.95 (m, 2H), 1.72 (m, 4H), 1.27 (m, 3H), 1.11 (d, J = 7.0, 18H) |
| 91 | (chromene with TIPSO, gem-dimethyl, 2-thienyl substituent) | 414.20 | 415.02 | ¹H NMR (CDCl₃, 300 MHz) 7.22 (m, 1H), 7.02 (d, J = 2.0, 1H), 7.01 (s, 1H), 6.91 (d, J = 7.5, 1H), 6.53 (s, 1H), 6.46 (d, J = 2.3, 1H), 6.43 (s, 2H), 1.62 (s, 6H), 1.28 (m, 3H), 1.11 (d, J = 7.0, 18H) |

TABLE 1-continued

| Compound | Structure | Molecular weight | MS analysis Value (Molecular weight +H⁺) | NMR |
|---|---|---|---|---|
| 92 | (TIPSO-substituted chromene spirocyclopentane with thiophene) | 440.22 | 441.13 | ¹H NMR (CDCl₃, 300 MHz) 7.19 (m, 1H), 6.99 (t, J = 5.0, 3.6, 1H), 6.94 (d, J = 2.9, 1H), 6.87 (d, J = 8.1, 1H), 6.55 (s, 1H), 6.41 (dd, J = 8.1, 2.3, 1H), 6.38 (d, J = 1.9, 1H), 2.16 (m, 2H), 2.03 (m, 4H), 1.72 (br s, 2H), 1.26 (m, 3H), 1.10 (d, J = 7.0, 18H) |
| 93 | (TIPSO-substituted 2,2-dimethyl chromene with pyridine) | 409.24 | 410.17 | ¹H NMR (CDCl₃, 300 MHz) 8.60 (d, J = 0.6, 1H), 8.56 (dd, J = 4.4, 1.6, 1H), 7.62 (dt, J = 6.1, 1.9, 1H), 7.30 (d, J = 7.2, 1H), 6.93 (dd, J = 7.9, 1.3, 1H), 6.49 (d, J = 2.4, 1H), 6.45 (s, 1H), 6.3 (s, 1H), 1.53 (s, 6H), 1.28 (m, 3H), 1.12 (d, J = 7.0, 18H) |
| 94 | (TIPSO-substituted chromene spirocyclopentane with pyridine) | 435.26 | 436.22 | ¹H NMR (CDCl₃, 300 MHz) 8.56 (m, 2H), 7.58 (d, J = 6.1, 1H), 7.26 (dd, J = 7.6, 5.1, 1H), 6.93 (d, J = 8.0, 1H), 6.45 (dd, J = 8.3, 2.4, 1H), 6.43 (s, 1H), 6.38 (s, 1H), 2,20 (m, 2H), 1.92 (m, 2H), 1.71 (m, 4H), 1.27 (m, 3H), 1.11 (d, J = 7.0, 18H) |
| 95 | (methoxy, OH-substituted 2,2-dimethyl chromene with chloro-methylphenyl) | 330.81 | | ¹H NMR (CDCl₃, 500 MHz): δ 7.22 (d, J = 2.0, 1H), 7.18 (dd, J = 8.0 and 2.0, 1H), 7.06 (d, J = 8.0, 1H), 6.32 (d, J = 8.5, 1H), 6.08 (d, J = 8.5, 1H), 3.86 (s, 3H), 2.13 (s, 3H), 1.56 (s, 3H), 1.52 (s, 3H) |

TABLE 1-continued

| Compound | Structure | Molecular weight | MS analysis Value (Molecular weight +H$^+$) | NMR |
|---|---|---|---|---|
| 96 | 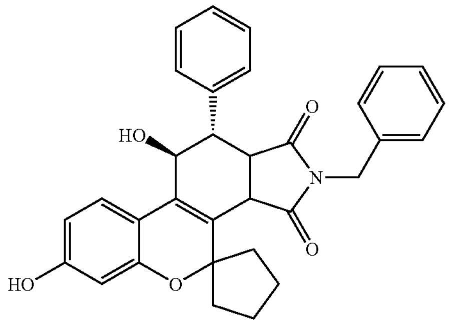 [SMILES: O=C1C2C3=C(c4ccc(O)cc4OC34CCCC4)[C@@H](O)[C@H](c3ccccc3)C2C(=O)N1Cc1ccccc1] | 507.58 | | $^1$H NMR (500 MHz, DMSO-d$_6$/CDCl$_3$): δ 9.43 (s, 1H), 7.18-7.07 (m, 7H), 7.02-7.01 (m, 2H), 6.89-6.88 (m, 2H), 6.35 (dd, J = 8.5 and 2.5, 1H), 6.27 (d, J = 2.5, 1H), 5.43 (d, J = 6.0, 1H), 4.71 (dd, J = 6.0 and 1.5, 1H), 4.08 (d, J = 7.0, 1H), 3.92-3.81 (AB q, J$_{AB}$ = 14.8, 2H), 3.66 (dd, J = 7.5 and 6.5, 1H), 3.53 (dd, J = 6.0 and 1.5, 1H), 2.63-2.22 (m, 1H), 2.17-2.13 (m, 1H), 2.07-2.00 (m, 1H), 1.96-1,87 (m, 2H), 1.81-1.69 (m, 3H) |

Experimental Example 1 to 12

Inhibition Activity

The inhibition activity of the compounds in Table 2 was measured by the following method.

The human cancer cell line (A549 lung carcinoma cell, Hela adenocarcinoma cell, U266 myeloma cell) was obtained from American Type Culture Collection (Manassas, Va. USA) and maintained in complete medium [RPMI. 1640 supplemented with heat-inactivated 10% FBS (USP, Austin, Tex., USA) and with 1% antibiotic-antimycotic solution (USP, Austin, Tex., USA)]. The cells were maintained in a humidified atmosphere of 5% $CO_2$ and 95% air at 37° C., and cultured in T75 Flask (Nalge Nune International, Naperville, Ind., USA).

Cell viability was measured by a cell counting kit (CCK-8 assay, Dojindo, Tokyo, Japan), and the experimental procedure is based on the manufacturer's manual. The cells were cultured into 96-well plates at a density of 2×10$^4$ cells/well for 24 hours, followed by the treatment of the compounds of the present invention at various concentrations. After 24 h incubation with compounds, 10 μl of WST-8 solution (2-(2-methoxy-4-nitrophenyl)-3(4-nitrophenyl)-5-(2,4-disulfophenyl)-2H-tetrazolium, (Sigma-Aldrich Chemical Co., St. Louis, Mo., USA)) was added to each well, and plates were incubated for additional 2 hours at 37° C. The absorbance of each well at 450 nm was measured with a reference at 630 nm using a Bio-Tek model ELx800™ microplate reader (Bio-Tek Instruments, Inc., Winooski, Vt., USA). The percentage of cell viability was calculated by following Mathematical Equation 1. Results were plotted as cell viability versus concentration of tested compound using Origin pro 7.0 (OriginLab Co., North Hampton, Mass., USA) (X=concentration of tested compound, Y=cell viability), and IC$_{50}$ value was calculated using non-linear regression analysis (exponential function of following mathematical equation 2), which is shown in the following Table 2.

% cell viability=(mean absorbance in test wells)/(mean absorbance in control well)×100  [Mathematical Equation 1]

$Y=Ae^{-t/x}$  [Mathematical Equation 2]

TABLE 2

| Experimental Example | Formula | R | R$_1$ | R$_2$ | R$_3$ | R$_4$ | Y | Z | X | IC$_{50}$/μM (A549) |
|---|---|---|---|---|---|---|---|---|---|---|
| 1 | 2 | b | Ph | Bn | — | — | C3—OH | — | CH | 1.0 |
| 2 | 3 | a | Ph | Bn | — | — | C3—OH | — | — | 33.5 |
| 3 | 3 | b | Ph | Bn | — | — | C3—OH | — | — | 63.9 |
| 4 | 4 | b | Ph | Bn | — | — | C3—OH | — | CH | 28.6 |
| 5 | 7 | a | H | Ph | — | — | C3—OH | — | CH | 7.0 |
| 6 | 7 | b | H | Ph | — | — | C3—OH | — | CH | 11.1 |
| 7 | 7 | a | MeOCH$_2$ | Ph | — | — | C3—OH | — | CH | 30.0 |
| 8 | 7 | b | MeOCH$_2$ | Ph | — | — | C3—OH | — | CH | 6.5 |
| 9 | 7 | b | H | Ph | — | — | C3—OH | — | N | 39.2 |
| 10 | 5 | b | — | — | Bn | — | C3—OH | — | — | 157.2 |

TABLE 2-continued

| Experimental Example | Formula | R | $R_1$ | $R_2$ | $R_3$ | $R_4$ | Y | Z | X | $IC_{50}/\mu M$ (A549) |
|---|---|---|---|---|---|---|---|---|---|---|
| 11 | 9 | b | — | — | Bn | — | C3—OH | — | — | 25.9 |
| 12 | 6 | b | — | — | — | $mNO_2$—Ph | C3—OH | — | — | 53.4 | a represents that each R independently is methyl group, and
b represents that two of Rs together form —$CH_2(CH_2)_2CH_2$—.

As shown in Table 2, it was found that the compounds of the present invention exhibited a wide range of $IC_{50}$ values, in particular, the compound of Experimental Example 1 was excellent in inhibition activity ($IC_{50}$=1.0 μM).

On the other hand, as compared to the compound of Experimental Example 1, $IC_{50}$ values of the compounds of Experimental Example 2, Experimental Example 3, and Experimental Example 4 which are a set of molecules with the same substituents but different core skeletons, were 30 to 60 fold higher. From the results, it can be confirmed that the core skeleton, not the substituents are important for their biological activities.

Experimental Example 13

Further, Compound 95 in Table 1, which has benzopyran core and obtained by performing Suzuki coupling reaction, demonstrates excellent anticancer effects on the human cancer cell line such as Hela and U266 cell as well as A549 cell. The result was shown in Table 3.

TABLE 3

| Experimental | | $IC_{50}$ (after 72 hr treatment) | | |
|---|---|---|---|---|
| Example | Compound | Hela | U266 | A549 |
| 13 | 95 | 450 nM | 460 nM | 380 nM |

The compound has an agonistic effect of activating RAR-related orphan receptor α (RORα) which is a orphan nuclear receptor. RORα is a transcription factor which affects a variety of physiological functions. The research result that RORα is especially related with breast cancer and prostate cancer (S. M. Hill et al., *Mol. Cell. Endo.* 2001, 176, 111; S. M. Hill et al., *Cancer Letters* 2002, 179, 141; P. Limonta, *Int. J. Cancer* 2004, 112, 87.) has been reported.

Therefore, benzopyran derivatives, which are RORα agonists, are very interesting objects of study as anticancer agents.

Experimental Example 14

Derivation of Prostate Anticancer Agent Candidates

Androgen receptor (AR) playing a major role in prostate cancer is a nuclear receptor and is a protein which plays an important part in carcinogenesis and progress.

The prostate cancer cell line which expresses stably a luciferase reporter is cultured in a DMEM supplemented with 10% FBS and the medium is replaced by a new medium at an interval of two days. As the cell is grown to 70%, the cell is separated from the culture flask using 0.25% trypsin/EDTA and plated in 96-well plates again to come to a density of $1 \times 10^3$ cell.

At this time, the medium for suspending the cell is RPMI 1640 supplemented with 10% charcoal stripped FBS, and without phenol red. After 48 hours, 20 nM of dihydrotestosterone (DHT) of an androgen receptor agonist is treated and then the prepared compound is treated in 24 hours. After additional 24 hours, the expression of luciferase is measured by using a luciferase assay kit and a screening method is established so as to find androgen receptor antagonists.

In FIG. 1, the anticancer activity of Compound 96 demonstrates that it is almost analogous to that of bicalutamide currently used as a prostate anticancer agent.

Figure 2:
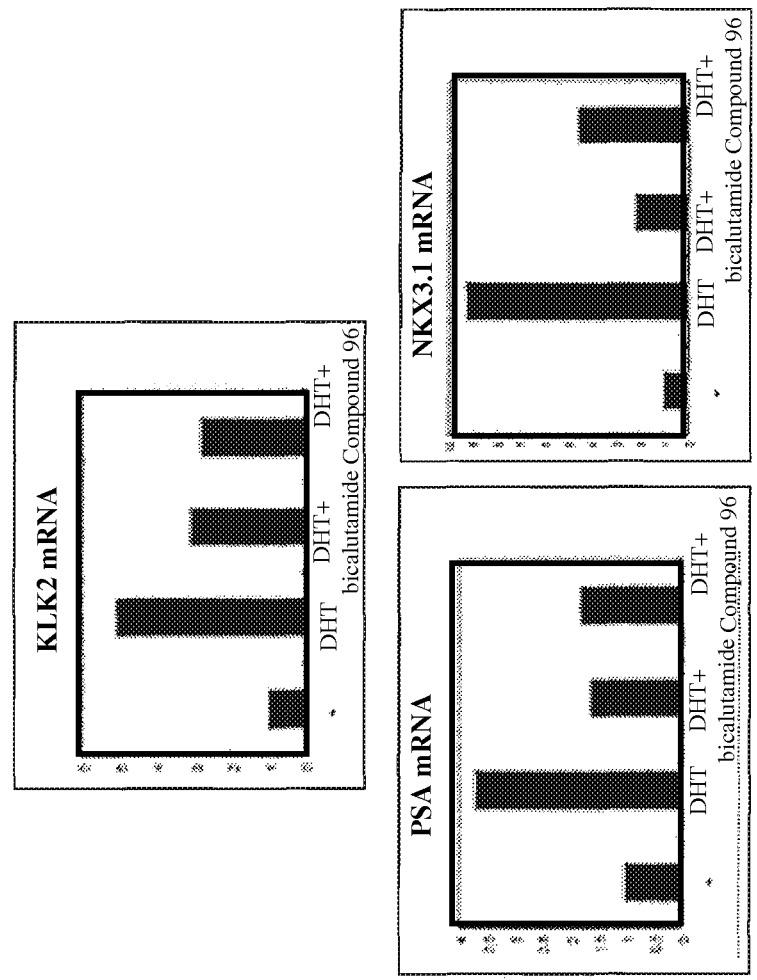
FIG. 2 shows an experimental result in mRNA level which demonstrates the effect of androgen receptor (AR) on target gene via RT-PCR amplification.
Figure 2:
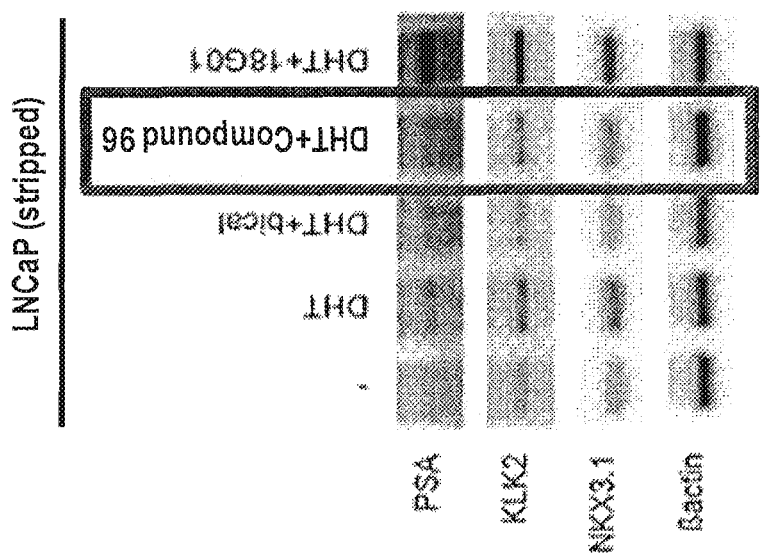

In FIG. 2, in the case of treating Compound 96, it can be found that mRNA amounts of prostate specific antigen (PSA), kallikrein-related peptidase 2 (KLK2), NK3 transcription factor related, locus 1 (NKX3-1), which are well-known target genes like bicalutamide, are decreasing.

Hereinbelow, Formulation Examples for the therapeutic agent of the present invention will be illustrated. However, these Formulation Examples are for the illustrative purpose only, and the present invention is not intended to be limited by these Formulation Examples.

Formulation 1. Preparation of Powder Formulation
Compound 36 20 mg
Lactose 100 mg
Talc 10 mg
The above ingredients are mixed, and charged in an air-tight package to prepare powder formulation.

Formulation 2. Preparation of Tablet Formulation
Compound 36 10 mg
Corn starch 100 mg
Lactose 100 mg
Magnesium stearate 2 mg
The above ingredients are mixed, and then tabletted according to a conventional preparation method to prepare tablet formulation.

Formulation 3. Preparation of Capsule Formulation
Compound 36 10 mg
Crystalline cellulose 3 mg
Lactose 14.8 mg
Magnesium stearate 0.2 mg
According to a conventional preparation method, the above ingredients are mixed and sealed in a gelatin capsule to prepare capsule formulation.

Formulation 4. Preparation of Injectable Formulation
Compound 36 10 mg
Mannitol 180 mg
Injectable distilled water 2974 mg
$Na_2HPO_4 \cdot 12H_2O$ 26 mg
According to a conventional preparation method, injectable formulation containing the above ingredients per one ampoule (2 ml) is prepared.

Formulation 5. Preparation of Liquid Formulation
Compound 36 20 mg
High-fructose corn syrup 10 g
Mannitol 5 g
Purified Water Predetermined Amount
According to a conventional preparation method, each ingredient is dissolved in the purified water, and a suitable amount of lemon flavor is added. Then, the above ingredients are mixed together, and the purified water is added to be 100 ml of total volume. The prepared solution is charged in a brown bottle, followed by sterilization to prepare liquid formulation.

What is claimed is:

1. A compound having benzopyran core, represented by any one of the following Formulae 1 to 5 or 7 to 9:

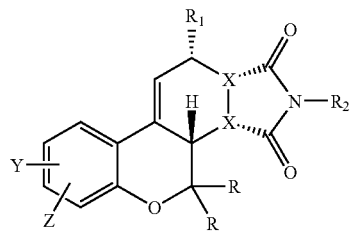

[Formula 1]

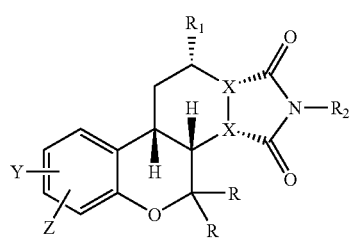

[Formula 2]

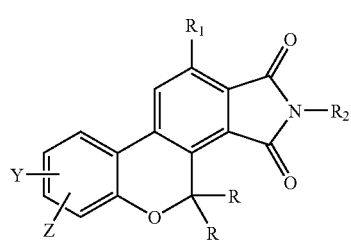

[Formula 3]

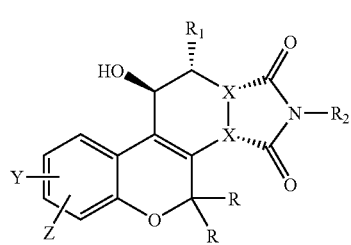

[Formula 4]

wherein in Formulae 1 to 4, each Y and Z independently are hydrogen; C1 to C6 linear or branched alkyl; hydroxy; protected hydroxy in the form of C3 to C9 linear or branched alkyl silyl ether; halogen; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, protected hydroxy in the form of C3 to C9 linear or branched alkyl silyl ether, halogen, amino, C1 to C4 alkylamino, C1 to C4 dialkylamino, acetyl and benzoyl, $R_1$ is hydrogen; methoxymethyl; C1 to C6 linear or branched alkyl; benzyl; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, halogen, amino, C1 to C4 alkylamino, C1 to C4 dialkylamino, acetyl and benzoyl, $R_2$ is hydrogen; hydroxy; C1 to C6 linear or branched alkyl; halogen; benzyl; C3 to C6 cycloalkyl; phenylamino; aminocarbonyl; methoxycarbonyl; C1 to C6 linear or branched carboxylic acid; thiophenylmethyl; N-benzylpiperidinyl; or phenyl that is substituted or unsubstituted with at least one substituent selected from the group consisting of C1 to C6 linear or branched alkyl, C1 to C6 linear or branched alkoxy, hydroxy, halogen, amino, C1 to C4 alkylamino, C1 to C4 dialkylamino, phenylamino, acetyl, benzoyl, phenyldiazo, carboxyl, benzoxazolyl, nitro, morpholinyl and $CF_3$, each R independently is methyl, or two of Rs together form —$CH_2(CH_2)_2CH_2$—, and X is CH or N;

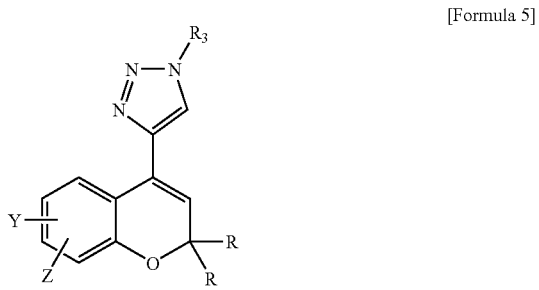

[Formula 5]

wherein in Formula 5, each Y and Z independently are hydrogen; C1 to C6 linear or branched alkyl; hydroxy; protected hydroxy in the form of C3 to C9 linear or branched alkyl silyl ether; halogen; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, protected hydroxy in the form of C3 to C9 linear or branched alkyl silyl ether, halogen, amino, C1 to C4 alkylamino, C1 to C4 dialkylamino, acetyl and benzoyl, $R_3$ is C1 to C8 linear or branched alkyl; C3 to C6 cycloalkylmethyl; pyridylmethyl; phenyl substituted or unsubstituted with at least one halogen; triazine substituted with methylsulfinyl or isopropylamino; C1 to C8 hydroxyalkyl; linear or branched carboxylic acid containing C1 to C8 heteromolecule; benzyl that is substituted or unsubstituted with at least one substituent selected from the group consisting of C1 to C6 linear or branched alkyl, C1 to C6 linear or branched alkoxy, methylthio, hydroxy, halogen, nitrile, acetyl, benzoyl and carboxylic acid;

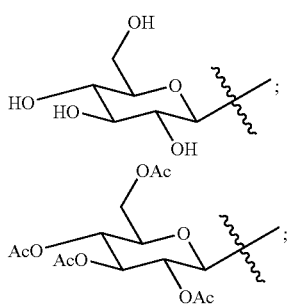

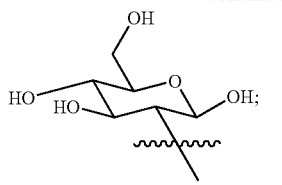

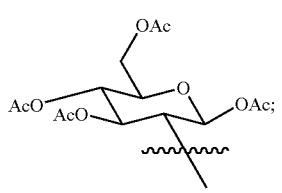

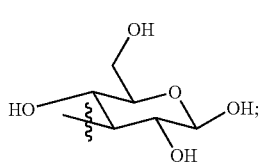

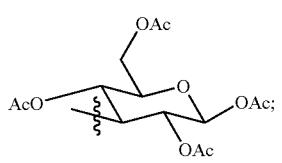

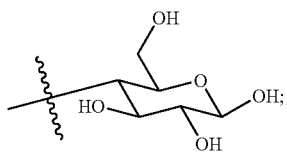

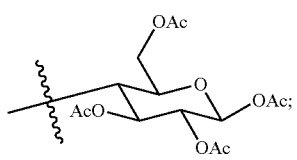

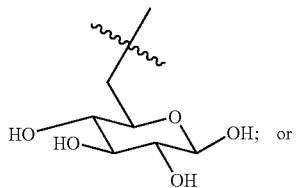

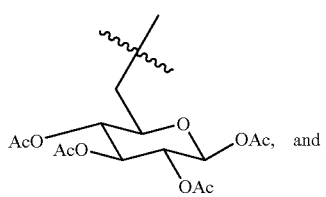

each R independently is methyl, or two of Rs together form —CH$_2$(CH$_2$)$_2$CH$_2$—;

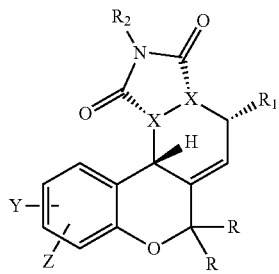

[Formula 7]

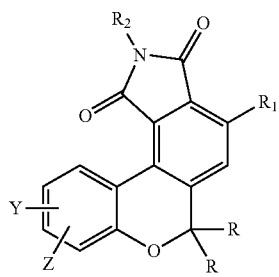

[Formula 8]

wherein in Formulae 7 and 8, each Y and Z independently are hydrogen; C1 to C6 linear or branched alkyl; hydroxy; protected hydroxy in the form of C3 to C9 linear or branched alkyl silyl ether; halogen; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, protected hydroxy in the form of C3 to C9 linear or branched alkyl silyl ether, halogen, amino, C1 to C4 alkylamino, C1 to C4 dialkylamino, acetyl and benzoyl, R$_1$ is hydrogen; methoxymethyl; C1 to C6 linear or branched alkyl; benzyl; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, halogen, amino, C1 to C4 alkylamino, C1 to C4 dialkylamino, acetyl and benzoyl, R$_2$ is hydrogen; hydroxy; C1 to C6 linear or branched alkyl; halogen; benzyl; C3 to C6 cycloalkyl; phenylamino; aminocarbonyl; methoxycarbonyl; C1 to C6 linear or branched carboxylic acid; thiophenylmethyl; N-benzylpiperidinyl; or phenyl that is substituted or unsubstituted with at least one substituent selected from the group consisting of C1 to C6 linear or branched alkyl, C1 to C6 linear or branched alkoxy, hydroxy, halogen, amino, C1 to C4 alkylamino, C1 to C4 dialkylamino, phenylamino, acetyl, benzoyl, phenyldiazo, carboxyl, benzoxazolyl, nitro, morpholinyl and CF$_3$, each R independently is methyl, or two of Rs together form —CH$_2$(CH$_2$)$_2$CH$_2$—, and X is CH or N;

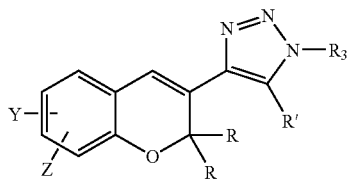

[Formula 9]

wherein in Formula 9, each Y and Z independently are hydrogen; C1 to C6 linear or branched alkyl; hydroxy; protected hydroxy in the form of C3 to C9 linear or branched alkyl silyl ether; halogen; C1 to C6 linear or branched alkoxy; or phenyl that is substituted or unsubstituted with at least one substituent selected from the group consisting of C1 to C6 linear or branched alkyl, C1 to C6 linear or branched alkoxy, hydroxy, protected hydroxy in the form of C3 to C9 linear or branched alkyl silyl ether, halogen, amino, C1 to C4 alkylamino, C1 to C4 dialkylamino, acetyl and benzoyl, $R_3$ is C1 to C8 linear or branched alkyl; C3 to C6 cycloalkylmethyl; pyridylmethyl; phenyl substituted or unsubstituted with at least one halogen; triazine substituted with methylsulfinyl or isopropylamino; C1 to C8 hydroxyalkyl; linear or branched carboxylic acid containing C1 to C8 heteromolecule; benzyl that is substituted or unsubstituted with at least one substituent selected from the group consisting of C1 to C6 linear or branched alkyl, C1 to C6 linear or branched alkoxy, methylthio, hydroxy, halogen, nitrile, acetyl, benzoyl and carboxylic acid;

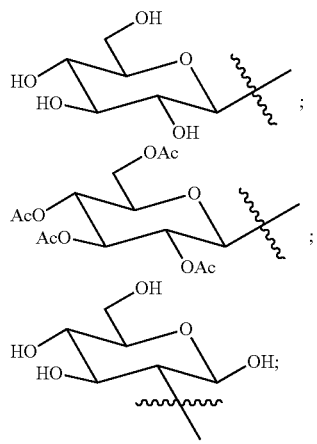

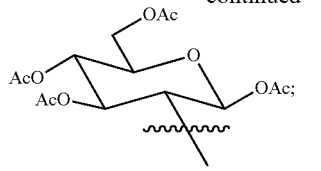

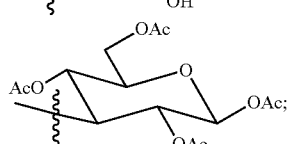

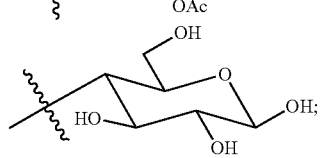

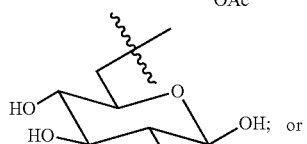

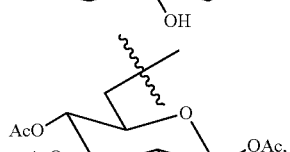

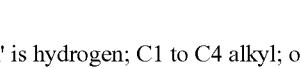

R' is hydrogen; C1 to C4 alkyl; or alkoxy, and each R independently is methyl, or two of Rs together form —CH$_2$(CH$_2$)$_2$CH$_2$—.

2. An anticancer composition comprising an effective amount of the compound having benzopyran core of claim 1 as an active ingredient.

3. The anticancer composition according to claim 2, wherein the cancer is prostate cancer.

* * * * *